(12) United States Patent
Patzer

(10) Patent No.: US 7,951,112 B2
(45) Date of Patent: May 31, 2011

(54) PUMP MODULE FOR USE IN A MEDICAL FLUID DISPENSING SYSTEM

(75) Inventor: Charles R. Patzer, Columbus, OH (US)

(73) Assignee: Smiths Medical ASD, Inc., St. Paul, MN (US)

( * ) Notice: Subject to any disclaimer, the term of this patent is extended or adjusted under 35 U.S.C. 154(b) by 707 days.

(21) Appl. No.: 11/749,313

(22) Filed: May 16, 2007

(65) Prior Publication Data

US 2008/0287872 A1   Nov. 20, 2008

(51) Int. Cl.
*A61M 37/00* (2006.01)
(52) U.S. Cl. ...................................................... 604/131
(58) Field of Classification Search .................. 604/131; 417/477.2
See application file for complete search history.

(56) References Cited

U.S. PATENT DOCUMENTS

| | | | |
|---|---|---|---|
| 1,727,049 A * | 9/1929 | Cobb | 417/491 |
| 2,311,851 A | 2/1943 | McClure | |
| 3,073,332 A | 1/1963 | Strader | |
| 3,216,355 A * | 11/1965 | Wanner | 74/55 |
| 3,744,936 A * | 7/1973 | Sadler | 417/536 |
| 3,985,652 A * | 10/1976 | Cooper | 210/97 |
| 4,065,230 A | 12/1977 | Gezari | |
| 4,084,606 A | 4/1978 | Mittleman | |
| 4,242,062 A * | 12/1980 | Pareja | 417/536 |
| 4,596,558 A | 6/1986 | Smith et al. | |
| 4,666,429 A | 5/1987 | Stone | |
| 4,819,684 A | 4/1989 | Zaugg et al. | |
| 5,147,333 A | 9/1992 | Raines | |
| 5,163,822 A * | 11/1992 | Koelln | 417/515 |
| 5,176,658 A | 1/1993 | Ranford | |
| 5,573,515 A | 11/1996 | Wilson et al. | |
| 5,716,111 A * | 2/1998 | Schenk et al. | 303/116.4 |
| 5,800,397 A | 9/1998 | Wilson et al. | |
| 5,882,343 A | 3/1999 | Wilson et al. | |
| 6,059,747 A | 5/2000 | Bruggeman et al. | |
| 6,099,476 A | 8/2000 | Devos et al. | |
| 6,221,045 B1 | 4/2001 | Duchon et al. | |
| 6,344,030 B1 | 2/2002 | Duchon et al. | |
| 6,579,079 B2 * | 6/2003 | Krevald | 417/510 |
| 6,626,862 B1 | 9/2003 | Duchon et al. | |
| 6,656,157 B1 | 12/2003 | Duchon et al. | |
| 6,866,654 B2 | 3/2005 | Callan et al. | |

(Continued)

FOREIGN PATENT DOCUMENTS

WO    9320864    10/1993

(Continued)

*Primary Examiner* — Nicholas D Lucchesi
*Assistant Examiner* — Diva Ranade
(74) *Attorney, Agent, or Firm* — Wood, Herron & Evans, LLP

(57) ABSTRACT

A pump module is provided for use in a medical fluid dispensing system that includes a pump body made of a non-compliant material and first and second pump chambers formed in the body. Each of the chambers has a first, open end and an opposite, closed end. The pump module further includes first and second pistons in the first and second pump chambers, respectively. At least one fluid inlet and a fluid outlet are selectively in fluid communication with the first and second pump chambers. Each of the pistons extends through the open end of a respective one of the pump chambers, with each of the pistons being operably translatable within the pump chamber toward and away from the closed end of the chamber. The pistons are translatable independently of one another.

26 Claims, 13 Drawing Sheets

U.S. PATENT DOCUMENTS

| | | |
|---|---|---|
| 2002/0183616 A1 | 12/2002 | Toews et al. |
| 2003/0059323 A1 | 3/2003 | Krevald |
| 2004/0101426 A1* | 5/2004 | Wahlberg .................. 417/492 |
| 2004/0143212 A1 | 7/2004 | Trombley et al. |
| 2005/0096627 A1 | 5/2005 | Howard |
| 2008/0097291 A1* | 4/2008 | Hanson et al. ............ 604/93.01 |
| 2008/0135126 A1* | 6/2008 | Lemme ........................ 141/8 |
| 2008/0294040 A1* | 11/2008 | Mohiuddin et al. .......... 600/432 |
| 2009/0053086 A1* | 2/2009 | Navarro ..................... 417/493 |

FOREIGN PATENT DOCUMENTS

| | | |
|---|---|---|
| WO | 9702852 | 1/1997 |
| WO | 0136026 | 5/2001 |
| WO | 0158506 | 8/2001 |

* cited by examiner

PUMP MODULE FOR USE IN A MEDICAL FLUID DISPENSING SYSTEM

FIELD

The present invention relates generally to pumps, and more particularly to pump modules for use in medical fluid dispensing systems.

BACKGROUND

A variety of known pumps are used to dispense medical fluids. Syringes are widely used to dispense relatively small volumes of medical fluids, which can include highly concentrated medication. The maximum volume of syringes is typically about 60 ml. After this volume is dispensed, a caregiver must replace the depleted syringe to continue medication. Accordingly, syringes do not lend themselves to large volume applications such as the dispensing of large volumes of blood in various circumstances or the dispensing of high volumes of fluid, such as saline, to burn patients for example.

Syringes can be used in conjunction with syringe pumps that automatically operate the single plunger or piston of the syringe. Typically, the plunger tip is made of a soft, compliant rubber. When the plunger is pushed to dispense fluid, the tip is compressed and forced to the outer wall of the syringe. "Stiction" can then occur when the piston is moved again after being stationary, where "stiction" is a term known in the art derived from the ability to stick in combination with static and dynamic friction. In such an intermittent operation, the force required to overcome the "stiction" and start the piston moving can cause a relatively large bolus of fluid to be dispensed initially, which is undesirable.

Known pumps that are used in systems to dispense large volumes of medical fluids include peristaltic pumps, various diaphragm pumps, and single piston pumps. Although each type has been successfully used, they are subject to certain design and/or application challenges. For example, since the fluid flow passage in peristaltic pumps is normally open, fluid can be inadvertently supplied to the patient. This can occur if the tubing leading from a source of fluid, such as an IV bag, to the inlet portion of the pump is not clamped. Also, the continuous compression of the tubing defining the normally open flow path can result in tube fatigue, thereby necessitating replacement of the tube that adds to the operational cost of the system.

Peristaltic pumps are also affected by the hydraulic head height, resulting from the position of the source of fluid above the pump, which can result in further inaccuracies with the flowrate of the pump.

Large volume single piston pumps are known but do not exhibit fluid flow constancy. This is because a "dead time" occurs, for each pumping cycle, after the piston pumps a predetermined volume of fluid and the output valve is closed, the piston is retracted and the piston chamber is refilled with fluid. This lack of flow constancy is undesirable since the half-life of certain medications can be on the order of seconds. If the medical fluid isn't delivered to and absorbed by the patient within this time, the medical fluid may be ineffective for its intended use. Flow constancy is a particularly important consideration when high potency medical fluids are being dispensed.

Known diaphragm pumps used in large volume medical fluid dispensing systems include those having a single elastomeric diaphragm and an associated piston to deform the diaphragm and dispense the medical fluid. Diaphragm pumps of this type can also include elastomeric check valves that communicate with the pump inlet and outlet ports. The compliant nature of these check valves can lead to variations in the breaking pressure of the valves, i.e., the pressures required to open or close the valves, which in turn can result in flowrate accuracy issues. A lack in flow constancy due to fluctuations in flowrate of the medical fluid being delivered is undesirable for the same reasons discussed previously with respect to the lack of flow constancy caused by "dead time." Another challenge associated with pumps having elastomeric diaphragms, is that the diaphragm(s) deform during the fill cycle and store potential energy. This energy is released during the pumping cycle, which can cause a relatively large bolus of fluid to be dispensed initially. This temporary spike in fluid flowrate also adversely affects flow constancy and is therefore undesirable.

Another known diaphragm pump used to dispense large volumes of medical fluids includes two elastomeric diaphragms that are pumped in alternating fashion. This pump does not include elastomeric check valves and the associated challenges. However, as with the single piston diaphragm pump, the compliant, elastomeric diaphragms are pressurized during the fluid fill cycle causing them to deform and store energy. Accordingly, when the corresponding output valve is opened at the beginning of the pumping cycle, a relatively large bolus of fluid can be dispensed, even without the associated piston moving, which is undesirable.

Another challenge associated with known large volume medical fluid pumps in general is the susceptibility to the formation of air bubbles in the fluid system and the typical requirement of caregiver intervention to "prime" the pump to eliminate the undesirable air bubbles. Air bubbles can be formed in the fluid delivery systems as a result of pump cavitation or "outgassing" that can occur when the temperature of the fluid is raised. Once air bubbles are detected in the delivery system the pump typically shuts down and triggers an alarm advising a caregiver of a problem. The time it takes for the caregiver to remedy the problem results in an interruption in the delivery of medical fluid to the patient. Spurious alarms result in a waste of caregiver time as well as an interruption in fluid delivery to the patient.

Yet another challenge associated with medical fluid pumps is the requirement to replace the portion of the pump that is exposed to the fluid after a predetermined, relatively short period of time as a result of hospital procedures associated with infection control. This replacement must be accomplished in an expeditious and cost effective manner.

It is therefore desirable to provide a pump having a replaceable pump module for use in medical fluid dispensing systems, which can be used in small and large volume fluid applications and overcomes the disadvantages associated with known pumps used in medical fluid dispensing systems.

SUMMARY

In view of the foregoing and by virtue of the present invention, a pump module is provided for use in a medical fluid dispensing system comprising a pump body made of a non-compliant material and first and second pump chambers formed in the body. Each of the chambers has a first, open end and an opposite, closed end. The pump module further includes first and second pistons in the first and second pump chambers, respectively. At least one fluid inlet is selectively in fluid communication with the first and second pump chambers. A fluid outlet is selectively in fluid communication with the first and second pump chambers. Each of the pistons extends through the open end of a respective one of the pump chambers, with each of the pistons being operably translatable within the respective one of the pump chambers toward and away from the closed end of the respective one of the pump chambers. The pistons are translatable independently of one another.

In other embodiments, the pump module can include one or more of the following features. The first and second pistons can be translatable and rotatable within the first and second pump chambers, respectively. The at least one fluid inlet can comprise a single fluid inlet. The first piston can be rotatable to a first angular orientation wherein the single fluid inlet is in fluid communication with the first pump chamber and can be rotatable to a second angular orientation wherein the fluid outlet is in fluid communication with the first pump chamber. The second piston can be rotatable to a first angular orientation wherein the single fluid inlet is in fluid communication with the second pump chamber and can be rotatable to a second angular orientation wherein the fluid outlet is in fluid communication with the second pump chamber. In this embodiment, each of the pistons can include a longitudinally extending channel formed therein and in fluid communication with a corresponding one of the pump chambers, with each of the channels being selectively in fluid communication with the at least one fluid inlet and the fluid outlet.

The first and second pistons can be disposed in opposing relationship with one another and the body can include a transverse wall separating the first and second pump chambers. Alternatively, the pistons can be disposed in a side-by-side relationship and the pump body can include a pair of laterally spaced cylinders formed therein, with each of the cylinders defining one of the pump chambers.

The at least one fluid inlet can comprise a single fluid inlet, defined by an inlet manifold. Alternatively, the at least one fluid inlet can comprise first and second fluid inlets. In this event, the pump module can comprise first and second inlet manifolds, with each defining one of the first and second fluid inlets. In another embodiment, the pump module can comprise a manifold defining the at least one fluid inlet and the fluid outlet.

In some embodiments, the pump module can include rotatable inlet and outlet valves, with the inlet valve being rotatable to a first angular orientation wherein the single fluid inlet is in fluid communication with the first pump chamber and is rotatable to a second angular orientation wherein the single fluid inlet is in fluid communication with the second pump chamber. Similarly, the outlet valve can be rotated to first and second angular orientations wherein the fluid outlet is in fluid communication with the first and second pump chambers, respectively. In these embodiments, the pistons are not rotatable.

The pump module can further comprise a pair of porous air filters, with each of the porous air filters comprising a hydrophobic material and each being in fluid communication with one of the pump chambers. Each of the filters is operably effective for allowing any air entrained within a fluid being pumped out of a corresponding one of the pump chambers to pass through the filter and discharge from the pump module.

According to a second aspect of the present invention, a pump is provided comprising a pump body made of a non-compliant material, with first and second pump chambers formed in the body. Each of the chambers have a first, open end and an opposite, closed end. The pump further includes first and second pistons in the first and second pump chambers, respectively; a fluid inlet selectively in fluid communication with the first and second pump chambers; and a fluid outlet selectively in fluid communication with the first and second pump chambers. The pump also includes first and second linear actuators coupled to the first and second pistons, respectively, wherein each of the pistons extends through the open end of a respective one of the pump chambers. The first linear actuator is operable for translating the first piston within the first pump chamber toward and away from the closed end of the first pump chamber. The second linear actuator is operable for translating the second piston within the second pump chamber toward and away from the closed end of the second pump chamber. The first and second linear actuators are operable independently of one another wherein the first and second pistons are translatable independently of one another.

In other embodiments, the pump of the present invention can include one or more of the following features. The pump can further include first and second rotational actuators and these actuators can be mechanically coupled to the first and second pistons, respectively. In this event, the pistons are translatable and rotatable within the corresponding pump chamber. The first rotational actuator is operable for rotating the first piston to a first angular orientation wherein the fluid inlet is in fluid communication with the first pump chamber and is operable for rotating the first piston to a second angular orientation wherein the first pump chamber is in fluid communication with the fluid outlet. The second rotational actuator is operable for rotating the second piston to a first angular orientation wherein the fluid inlet is in fluid communication with the second pump chamber and is operable for rotating the second piston to a second angular orientation wherein the fluid outlet is in fluid communication with the second pump chamber.

In another embodiment, the pump can include an inlet valve, a first rotational actuator mechanically coupled to the inlet valve, an outlet valve, and a second rotational actuator mechanically coupled to the outlet valve. The first rotational actuator is operable for rotating the inlet valve to a first angular orientation wherein the fluid inlet is in fluid communication with the first pump chamber and is operable for rotating the inlet valve to a second angular orientation wherein the fluid inlet is in fluid communication with the second pump chamber. The second rotational actuator is operable for rotating the outlet valve to a first angular orientation wherein the fluid outlet is in fluid communication with the first pump chamber and is operable for rotating the outlet valve to a second angular orientation wherein the fluid outlet is in fluid communication with the second pump chamber.

According to a third aspect of the present invention, a system is provided for dispensing medical fluids intravenously to a patient comprising a pump and a programmable controller, wherein the pump comprises: a pump body made of a non-compliant material; first and second pump chambers formed in the body, each of the chambers having a first, open end and an opposite, closed end; first and second pistons in the first and second pump chambers, respectively; a fluid inlet selectively in fluid communication with the first and second pump chambers; a fluid outlet selectively in fluid communication with the first and second pump chambers; and first and second linear actuators coupled to the first and second pistons, respectively. Each of the pistons extends through the open end of a respective one of the pump chambers with the first linear actuator being operable for translating the first piston within the first pump chamber toward and away from the closed end of said first pump chamber and with the second linear actuator being operable for translating the second piston within the second pump chamber toward and away from the closed end of the second pump chamber. The first and second linear actuators are controlled independently of one another by the programmable controller such that the first and second pistons are translatable independently of one another.

In other embodiments, the system can include one or more of the following features. A first rotational actuator can be mechanically coupled to the first piston and a second rotational actuator can be mechanically coupled to the second piston. The first and second rotational actuators are controlled independently of one another and this can be done with the controller.

In other embodiments, the system can include inlet and outlet valves, a first rotational actuator mechanically coupled to the inlet valve, and a second rotational actuator mechanically coupled to the outlet valve. The first and second rotational actuators are controlled independently of one another and this can be done with the controller.

According to a fourth aspect of the present invention, a method is provided for pumping fluid in a medical fluid dispensing system comprising the steps of providing a pump module having a pump body made of a non-compliant material, with the pump body having first and second pump chambers formed therein, each having a first, open end and an opposite, closed end, with the pump module further comprising a fluid inlet and a fluid outlet, each selectively in fluid communication with the first and second pump chambers, and with the pump module further comprising first and second pistons in the first and second pump chambers, respectively. The method further includes providing first and second linear actuators, the first linear actuator being mechanically coupled to the first piston and the second linear actuator being mechanically coupled to the second piston. The method further includes translating the first and second pistons with the corresponding linear actuator within the respective one of the pump chambers toward and away from the closed end of the respective one of the pump chambers and operating the linear actuators independently of one another.

In other embodiments, the method can include one or more of the following steps. The pump can further include a first rotational actuator mechanically coupled to the first piston and a second rotational actuator mechanically coupled to the second piston, with the method further comprising rotating one of the pistons with the corresponding rotational actuator to a first angular orientation wherein the fluid inlet is in fluid communication with the corresponding pump chamber and retracting the one of the pistons within the corresponding pump chamber to at least partially fill the corresponding pump chamber with medical fluid. In this embodiment, the method can further include subsequently rotating the one of the pistons to a second angular orientation wherein the fluid outlet is in fluid communication with the corresponding one of the pump chambers and extending the one of the pistons within the corresponding pump chamber to pump the medical fluid out of the corresponding pump chamber and through the medical outlet.

In another embodiment, the pump can further include an inlet valve, a first rotational actuator mechanically coupled to the inlet valve, an outlet valve and a second rotational actuator mechanically coupled to the outlet valve, with the method further comprising rotating the inlet valve to a first angular orientation wherein the fluid inlet is in fluid communication with one of the pump chambers and retracting the corresponding piston within the one of the pump chambers to at least partially fill the one of the pump chambers with medical fluid. In this embodiment, the method can further include subsequently rotating the inlet valve to a second angular orientation wherein the fluid inlet is fluidicly uncoupled with the one of the pump chambers and rotating the outlet valve to an angular orientation wherein the fluid outlet is in fluid communication with the one of the pump chambers and extending the corresponding piston within the one of the pump chambers to pump the medical fluid out of the one of the pump chambers and through the fluid outlet.

DRAWINGS

These and other features, aspects and advantages of the present invention will become better understood with regard to the following description, appended claims and accompanying drawings wherein:

DESCRIPTION

Figure 1:
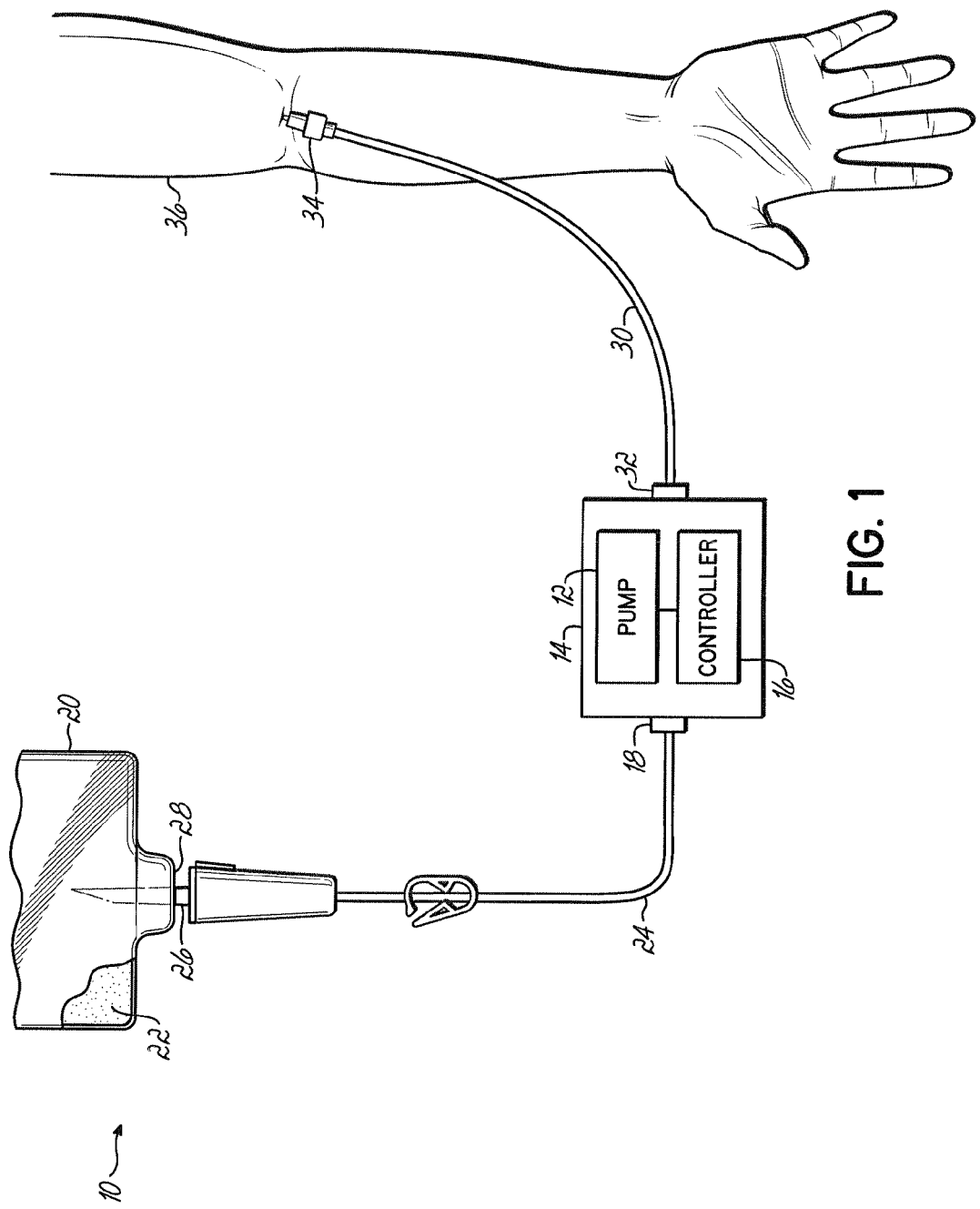
FIG. 1 is a schematic illustration of a system for dispensing medical fluids intravenously to a patient, which incorporates a pump according to the principles of the present invention.

Referring now to the drawings, FIG. 1 illustrates a system 10 for dispensing medical fluids intravenously to a patient, with system 10 incorporating a pump, indicated schematically at 12, in accordance with the principles of the present invention. Pump 12 can be disposed within an enclosure, illustrated schematically at 14, and can be electrically coupled to a controller 16 that can control the operation of pump 12. Controller 16 can also be disposed within the enclosure 14.

A fluid inlet (not shown in FIG. 1) of pump 12 is fluidicly coupled to a source of fluid to be dispensed which can comprise a bag 20, commonly referred to as an IV bag, containing a fluid 22 therein. The fluid 22 can comprise a variety of medications and can also include other fluids, such as saline solution, as known in the art. The system 10 can further include a first section of tubing 24 that can comprise a single piece of tubing or multiple pieces of interconnected tubing. Tubing 24 can pass through a tubing inlet 18 of enclosure 14, and be fluidicly coupled to a fluid inlet (not shown in FIG. 1) of pump 12 by one or more conduits and fluid connectors (not shown). The opposite end of tubing 24 can terminate in a spike 26 adapted to pierce a port 28 of the IV bag 20.

System 10 can also include a second section of tubing 30 that can comprise a single piece of tubing or multiple pieces of interconnected tubing. Tubing 30 can pass through a tubing outlet 32 of enclosure 14, and be fluidicly coupled to a fluid outlet (not shown in FIG. 1) of pump 12 by one or more conduits and fluid connectors (not shown). The opposite end of tubing 30 can terminate in a catheter 34 inserted intravenously into an arm 36 of a patient. In at least one embodiment, a second source of fluid (not shown) can also be fluidicly coupled to a pump in accordance with the principles of the present invention as subsequently discussed.

FIGS. 2-6 illustrate a pump module 50 according to one embodiment of the present invention. The module 50 includes a pump body 52 made of a non-compliant material. An example of a suitable material is a plastic material, such as a polycarbonate. As best seen in FIGS. 3A-3C, first 54 and second 56 pump chambers are formed in the pump body 52. Chamber 54 includes a first, open end 58 and an opposite, closed end 60. Similarly, pump chamber 56 includes a first, open end 62 and an opposite, closed end 64. The closed ends 60, 64 of pump chambers 54, 56 respectively can be defined by a transverse wall 66 formed in pump body 52 that separates pump chambers 54 and 56. The transverse wall 66 is made of the same non-compliant material as the remainder of pump body 52.

Figure 3A:
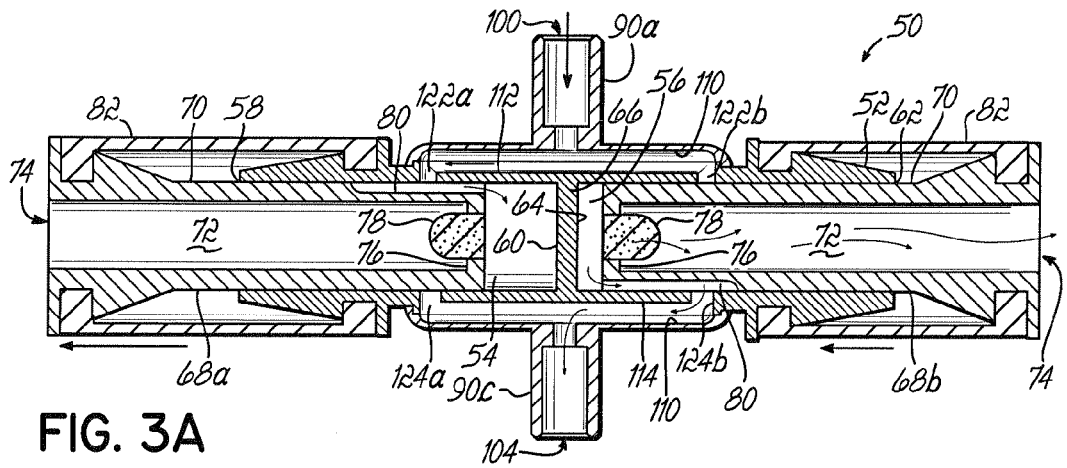
FIG. 3A is a cross-sectional view taken along line 3A-3A in FIG. 2 illustrating a first pump chamber being filled with fluid and fluid being pumped out of a second pump chamber.
Figure 3B:
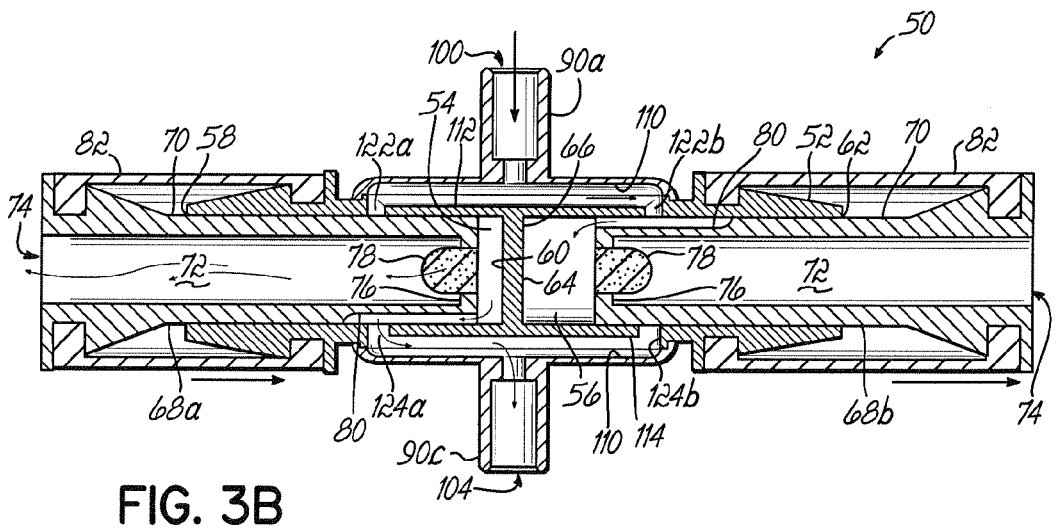
FIG. 3B is a cross-sectional view similar to FIG. 3A but with the second pump chamber being filled with fluid and with fluid being pumped out of the first pump chamber.
Figure 3C:
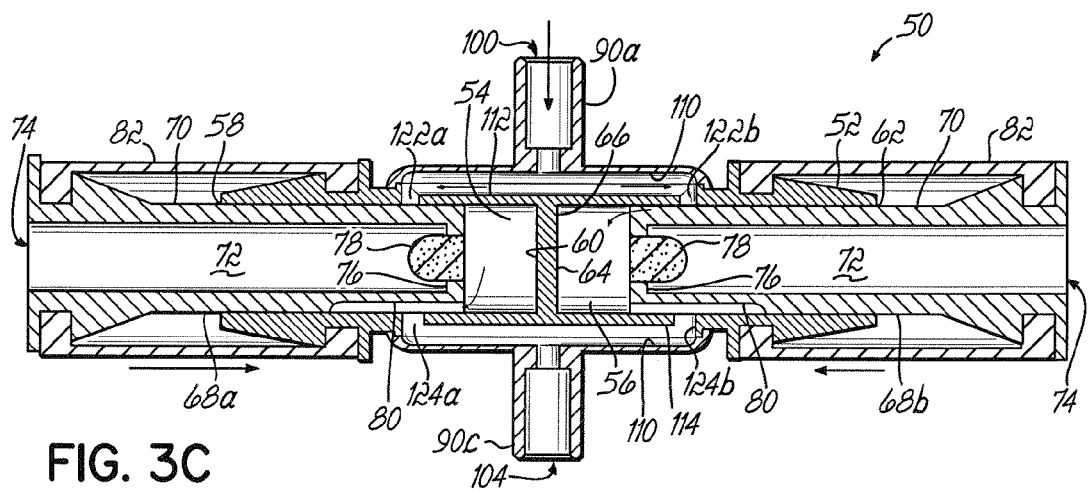
FIG. 3C is a cross-sectional view similar to FIG. 3A but with fluid being pumped out of both of the pump chambers.

Module 50 further includes a pair of pistons, designated as 68*a* and 68*b* that are disposed in the pump chambers 54 and 56, respectively. Pistons 68*a* and 68*b* can be made of high density polyethylene (HDPE) due to the lubricity of this material. However, pistons 68*a* and 68*b* can be made of other suitable materials. As shown in FIGS. 3A-3C, piston 68*a* extends through the open end 58 of pump chamber 54, while piston 68*b* extends through the open end 62 of pump chamber 56. Pistons 68*a*, 68*b* can have cylindrical portions 70. Each of the pistons 68*a*, 68*b* can include a hollow interior 72 and an open distal end 74. Each piston 68*a*, 68*b* further includes a wall 76 at a distal end thereof and each wall 76 can include an aperture formed therein to receive a porous air filter 78. Each of the air filters 78 is in fluid communication with one of the pump chambers 54, 56 and the hollow interior 72 of the corresponding one of pistons 68*a*, 68*b*. Each air filter 78 includes a hydrophobic material that is effective for permitting air to pass therethrough, but which repels water, as subsequently discussed in further detail. Each of the pistons 68*a*, 68*b* can include a longitudinally extending channel 80 formed therein that is in fluid communication with the corresponding one of the pump chambers 54, 56.

Piston 68*a* is translatable within pump chamber 54 toward and away from the closed end 60 of chamber 54 and is also rotatable within chamber 54 such that the longitudinally extending channel 80 can assume various angular orientations for a subsequently described purpose. Similarly, piston 68*b* is translatable within pump chamber 56 toward and away from the closed end 64 of chamber 56, and is also rotatable within chamber 56. As subsequently discussed, linear and rotational actuators are used to achieve the desired translation and rotation, respectively, of pistons 68*a* and 68*b*.

Pump module 50 can further include a pair of covers or seals 82, which can be used to prevent pistons 68*a*, 68*b* from being contaminated by the surrounding environment. As shown in FIGS. 3A-3C, each cover 82 can be disposed at one end in a circumferentially extending notch formed in pump body 52 and can be disposed at the opposite end thereof in a circumferentially extending notch formed in the corresponding one of pistons 68*a* and 68*b*. For ease of illustration, covers 82 are illustrated as having a substantially cylindrical exterior. However, in order to accommodate the translation of pistons 68*a*, 68*b* within the chambers 54 and 56, respectively, covers 82 can have a bellows-type configuration, or other suitable configuration, made of a material that permits longitudinal expansion and contraction. The covers 82 also permit the pistons 68a, 68b to rotate within chambers 54 and 56, respectively.

Figure 2:
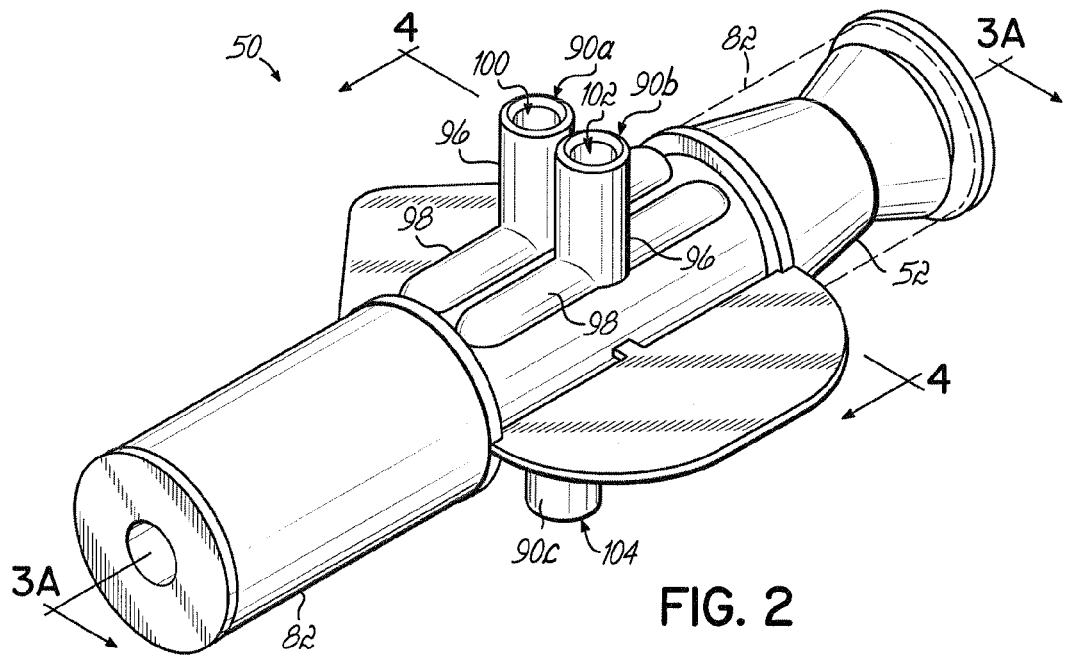
FIG. 2 is a perspective view of a pump module according to one embodiment of the present invention.
Figure 4:
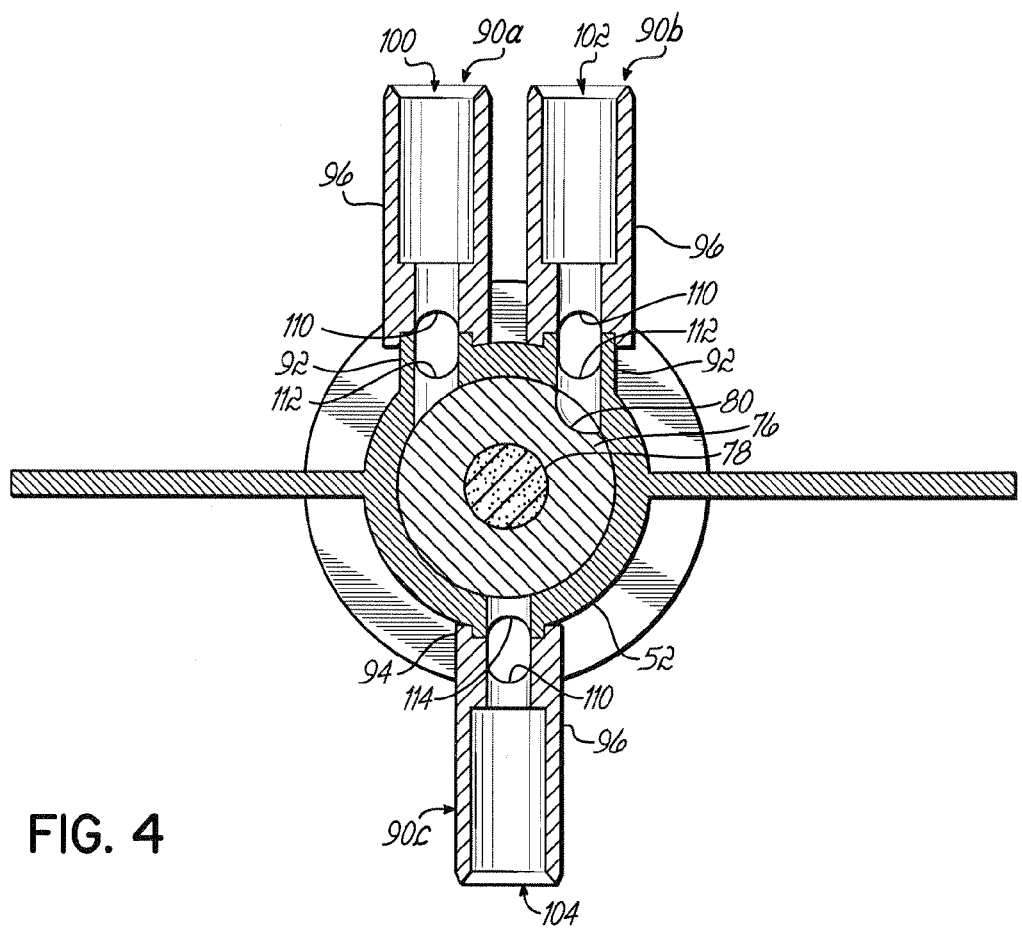
FIG. 4 is a cross-sectional view taken along line 4-4 in FIG. 2.
Figure 5:
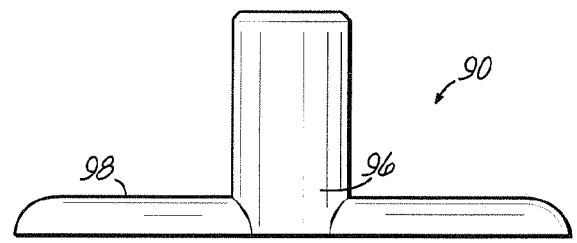
FIG. 5 is a side elevation view of one of the fluid manifolds shown in FIGS. 2-4.
Figure 6:
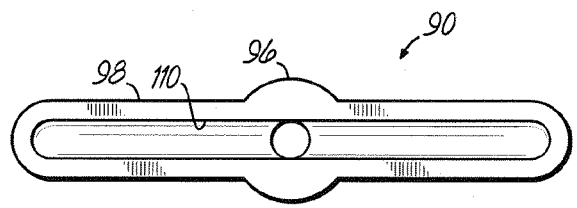
FIG. 6 is a bottom plan view of the manifold shown in FIG. 5.

Pump module 50 includes a plurality of manifolds 90, with one being illustrated in FIGS. 5 and 6. In the illustrated embodiment, module 50 includes two inlet manifolds designated 90a and 90b as shown in FIGS. 2 and 4 and an outlet manifold 90c. However, in other embodiments, one of the inlet manifolds 90a, 90b can be eliminated. Each of the manifolds 90 is secured to the pump body 52, which can be achieved in a variety of ways. In the illustrated embodiment, each of the inlet manifolds 90a, 90b is secured to an embossment 92 of pump body 52, while the outlet manifold 90c is secured to an embossment 94 of pump body 52. Each of the manifolds 90a, 90b and 90c can include a coupling portion 96 and an elongated portion 98 integral with the coupling portion 96. The coupling portions 96 are hollow, such that the coupling portion 96 of inlet manifold 90a defines a first fluid inlet 100, while the coupling portion 96 of inlet manifold 90b defines a second fluid inlet 102. The coupling portion 96 of outlet manifold 90c defines a fluid outlet 104.

The elongated portion 98 of each manifold 90a, 90b and 90c includes a fluid passage 110 formed therein. The fluid passage 110 of inlet manifold 90a is in fluid communication with fluid inlet 100 and the fluid passage 110 of inlet manifold 90b is in fluid communication with fluid inlet 102. Similarly, the passage 110 of outlet manifold 90c is in fluid communication with the fluid outlet 104. The fluid passage 110 of each inlet manifold 90a, 90b is aligned with a fluid passage 112 formed in pump body 52 and surrounded by one of the embossments 92. Accordingly, each of the fluid passages 112 is in fluid communication with the corresponding one of fluid inlets 100, 102. Similarly, the fluid passage 110 of outlet manifold 90c is aligned with a fluid passage 114 formed in pump body 52 and surrounded by the embossment 94. Accordingly, the fluid passage 114 is in fluid communication with fluid outlet 104.

Pump body 52 includes a plurality of apertures 122 formed therein, with a pair of the apertures 122 associated with each of the inlet manifolds 90a, 90b. Each aperture 122 (the two associated with manifold 90b are not shown) is in fluid communication with the corresponding fluid passage 112. As shown in FIGS. 3A-3C, pump body 52 includes apertures 122a and 122b, with each being in fluid communication with the fluid inlet 100. Aperture 122a opens into pump chamber 54 while aperture 122b opens into pump chamber 56. When the longitudinally extending channel 80 of piston 68a is aligned with aperture 122a as shown in FIG. 3A, the fluid inlet 100 is in fluid communication with pump chamber 54. Similarly, when the longitudinally extending channel 80 of piston 68b is aligned with aperture 122b, the fluid inlet 100 is in fluid communication with the pump chamber 56 as shown in FIG. 3B. In view of the foregoing, it may be appreciated that fluid inlets 100 and 102 are selectively in fluid communication with the pump chambers 54 and 56.

Pump body 52 also includes apertures 124a and 124b formed therein, with each in fluid communication with fluid passage 114 and therefore with the fluid outlet 104. Aperture 124a opens into pump chamber 54 and aperture 124b opens into pump chamber 56. Accordingly, when the longitudinally extending channel 80 of piston 68a is aligned with aperture 124a, pump chamber 54 is in fluid communication with fluid outlet 104. Similarly, when the channel 80 of piston 68b is aligned with aperture 124b, pump chamber 56 is in fluid communication with fluid outlet 104. In view of the foregoing, it may be appreciated that fluid outlet 104 is selectively in fluid communication with pump chambers 54 and 56.

Figure 7:
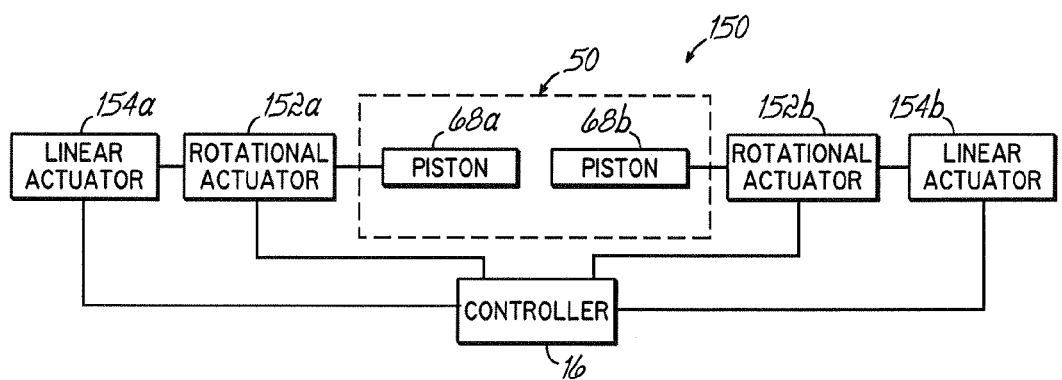
FIG. 7 is a schematic representation of a pump incorporating the pump module shown in FIGS. 1-6 and the corresponding control system.
Figure 8:
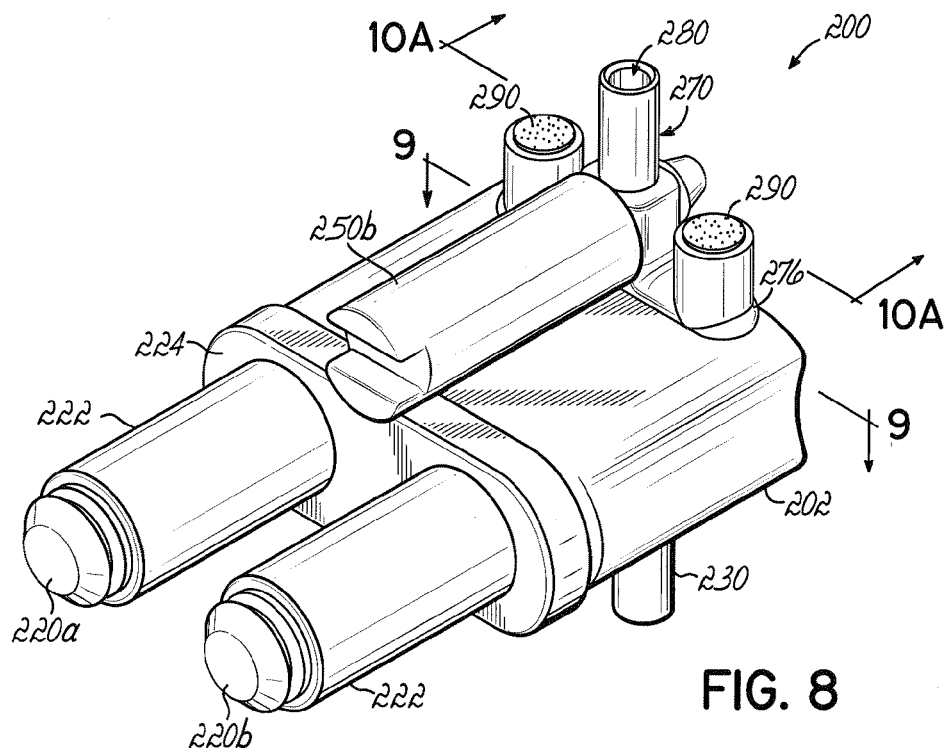
FIG. 8 is a perspective view of a pump module according to another embodiment of the present invention.

Pump module 50 can be included in a variety of pumps, such as pump 150 illustrated schematically in FIG. 7. In addition to pump module 50, pump 150 includes a pair of rotational actuators 152a, 152b and a pair of linear actuators 154a, 154b. The rotational actuators 152a, 152b are mechanically coupled to pistons 68a, 68b, respectively. Accordingly, rotational actuators 152a, 152b can be used to change the angular orientation of pistons 68a, 68b, respectively. Linear actuators 154a, 154b are mechanically coupled, which can be an indirect coupling as shown in FIG. 7 or a direct coupling, to pistons 68a, 68b respectively. Accordingly, actuator 154a can be used to translate piston 68a within pump chamber 54 and actuator 154b can be used to translate piston 68b within pump chamber 56. Actuators 154a, 154b can also be mechanically coupled to rotational actuators 152a, 152b, respectively, as shown in FIG. 7.

Each of the fluid inlets 100 and 102 can be fluidically coupled to a source of fluid which can be different, for instance with one of the inlets 100 and 102 being coupled to a medication and with the other being fluidicly coupled to a different medical fluid, such as saline for example. For purposes of illustration, the subsequent discussion of the operation of pump 150 will be explained in conjunction with fluid inlet 1 00. Fluid inlet 100 can be fluidicly coupled to a source of medical fluids such as bag 20 illustrated schematically in FIG. 1, having a fluid 22 contained therein. The fluid outlet 104 can be fluidicly coupled to a patient via a section of tubing and a catheter, such as tubing 30 and catheter 34 illustrated schematically in FIG. 1.

Rotational actuators 152a and 152b, and linear actuators 154a and 154b, are operated independently of one another and the operation of each of these actuators can be controlled by a programmable controller such as controller 16 illustrated schematically in FIGS. 1 and 7. Accordingly, pistons 68a and 68b are translatable and rotatable within pump chambers 54 and 56 respectively, independently of one another. This allows fluid to be pumped out of one or both of the chambers 54 and 56, at any given time. FIG. 3A illustrates one phase of operation of pump 150. In this phase, rotational actuator 152a rotates piston 68a to a first angular orientation wherein the longitudinal channel 80 of piston 68a is aligned with aperture 122a formed in pump body 52. Accordingly, fluid inlet 100 is in fluid communication with pump chamber 54 and fluid outlet 104 is fluidicly uncoupled with pump chamber 54. Piston 68a and rotational actuator 152a are retracted via linear actuator 154a, so that piston 68a is translated away from the transverse wall 66 of body 52, thereby filling at least a portion of pump chamber 54 with a medical fluid.

At the same time, fluid is being pumped out of chamber 56. This can be accomplished as follows. The rotational actuator 152b rotates piston 68b to an angular orientation such that channel 80 of piston 68b is aligned with aperture 124b as shown in FIG. 3A. This places the pump chamber 56 in fluid communication with the fluid outlet 104 and fluidicly uncouples fluid inlet 100 and pump chamber 56. Piston 68b is extended, or translated within pump chamber 56 toward the transverse wall 66 by linear actuator 154b. As piston 68b is extended toward the transverse wall 66, fluid is pumped out of pump chamber 56 and through fluid outlet 104. During this process, the inlet face of the porous filter 78 formed in the distal end 76 of piston 68b is forced against the fluid being pumped out of chamber 56. The fluid does not pass through filter 78 due to the presence of the hydrophobic material, but any air entrained within the fluid can pass through the filter 78 into the hollow interior 72 of piston 68b and can then discharge from module 50 through the open proximal end 74 of piston 68b. In order to ensure a constancy of fluid flow, piston 68a can be translated toward the transverse wall 66, just prior to the end of the pumping stroke of piston 68b. Accordingly, fluid can be pumped simultaneously out of both of the chambers 54 and 56 and through fluid outlet 104, as shown in FIG. 3C.

FIG. 3B illustrates a phase of operation where fluid is being pumped out of pump chamber 54 and through fluid outlet 104 while chamber 56 is being filled with fluid. This is achieved by aligning the channel 80 of piston 68a with aperture 124a thereby placing pump chamber 54 in fluid communication with the outlet 104 and by aligning the channel 80 of piston 68b with aperture 122b, thereby placing pump chamber 56 in fluid communication with the fluid inlet 100. Chamber 54 is fluidicly uncoupled with fluid inlet 100 and chamber 56 is fluidicly uncoupled with fluid outlet 104 during this phase of operation.

While pistons 68a and 68b are disposed in an opposing relationship with one another in pump module 50, in another embodiment (not shown) pistons 68a and 68b can be included in a pump module where pistons 68a and 68b are disposed in a side-by-side relationship with one another. This embodiment would include appropriate changes to the pump body and the inlet and outlet manifolds to accommodate this spatial relationship of pistons 68a and 68b. The operation, i.e., translation and rotation, of pistons 68a and 68b in this embodiment can be the same as discussed previously with reference to FIG. 7.

Figure 9A:
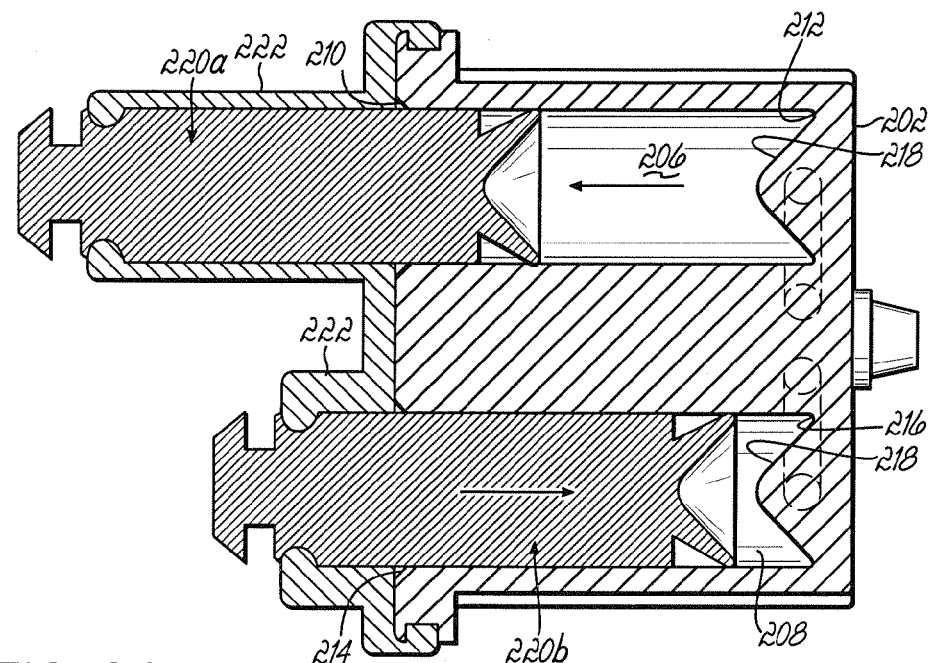
FIG. 9A is a cross-sectional view taken along line 9A-9A in FIG. 8 illustrating a first one of the included pistons being retracted wherein the corresponding pump chamber is at least partially filled with fluid, and illustrating the second piston being extended wherein fluid is being pumped out of the corresponding pump chamber.
Figure 9B:
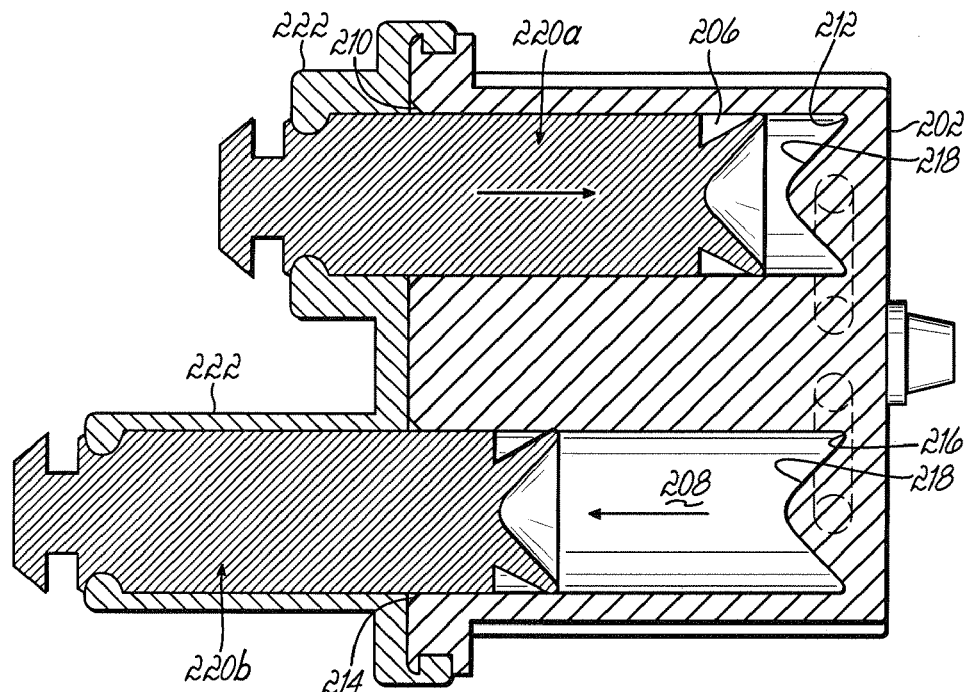
FIG. 9B is a cross-sectional view similar to FIG. 9A-9A, but with the first piston being extended and fluid being pumped out of the corresponding chamber and with the second piston being retracted wherein the corresponding chamber is at least partially filled with fluid.

FIGS. 8-13 illustrate a pump module 200 according to another embodiment of the present invention. The module 200 includes a pump body 202 made of a non-compliant material. An example of a suitable material is a plastic material, such as a polycarbonate. As best seen in FIGS. 9A and 9B, pump body 202 includes pump chambers 206 and 208 formed therein. Alternatively, chambers 206 and 208 can be defined by laterally spaced cylinders included in pump body 202. Chamber 206 includes a first, open end 210 and an opposite, closed end 212. Similarly, pump chamber 208 includes a first, open end 214 and an opposite, closed end 216. The closed ends 212, 216 of pump chamber 206, 208 respectively are defined by an end wall 218. End walls 218 can have a generally conical shape as shown in FIG. 9 to match a complementary shape of the distal ends of pistons 220a, 220b, which are included in module 200, or can have other shapes, such as a flat cylindrical shape for instance. The flared distal ends of pistons 220a, 220b provides flexibility that facilitates the moving contact with the inner surface of the chambers 206, 208 respectively, as pistons 220a, 220b are translated within chambers 206, 208. Pistons 220a, 220b can be made of HDPE, due to the lubricity of this material, or other suitable materials. The complementary shapes of end walls 218 and pistons 220a, 220b helps force fluid, and any air entrained therein, out of chambers 206, 208 during the corresponding pumping cycles. The end walls 218 are made of the same non-compliant material as the remainder of pump body 202.

As shown in FIG. 9, piston 220a extends through the open end 210 of chamber 206, while piston 220b extends through the open end 214 of chamber 208. Pistons 220a, 220b can have cylindrical portions. In other embodiments, pistons 220a and 220b can have a different configuration, such as a plurality of circumferentially spaced and longitudinally extending fins as shown in the subsequently discussed embodiment, in lieu of the cylindrical portions. This can be done for cost savings purposes, for example. Piston 220a is translatable within pump chamber 206 toward and away from the closed end 212 of chamber 206 and piston 220b is translatable within pump chamber 208 toward and away from the closed end 216 of chamber 208. Pump module 200 can further include a pair of covers or seals 222, which can be used to prevent pistons 220a, 220b from being contaminated by the surrounding environment. One end of each cover 222 can be integral with a base member 224 that is secured to pump body 202. Similar to the covers 82 of pump module 50, covers 222 are illustrated as having a substantially cylindrical exterior for ease of illustration. However, in order to accommodate the translation of pistons 220a, 220b within chambers 206 and 208, respectively, covers 222 can have a bellows-type configuration, or other suitable configuration, made of a material that permits longitudinal expansion and contraction.

Figure 10A:
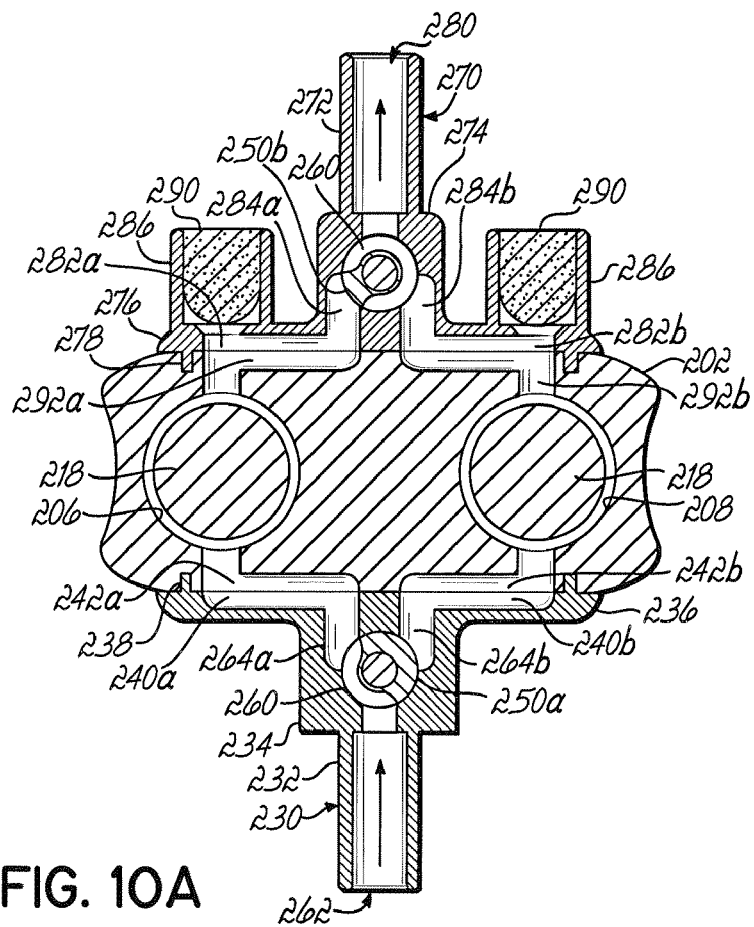
FIG. 10A is a cross-sectional view taken along line 10A-10A in FIG. 8 illustrating the inlet and outlet valves rotated to positions wherein a first pump chamber is being filled with fluid and fluid is being pumped out of a second pump chamber.
Figure 10B:
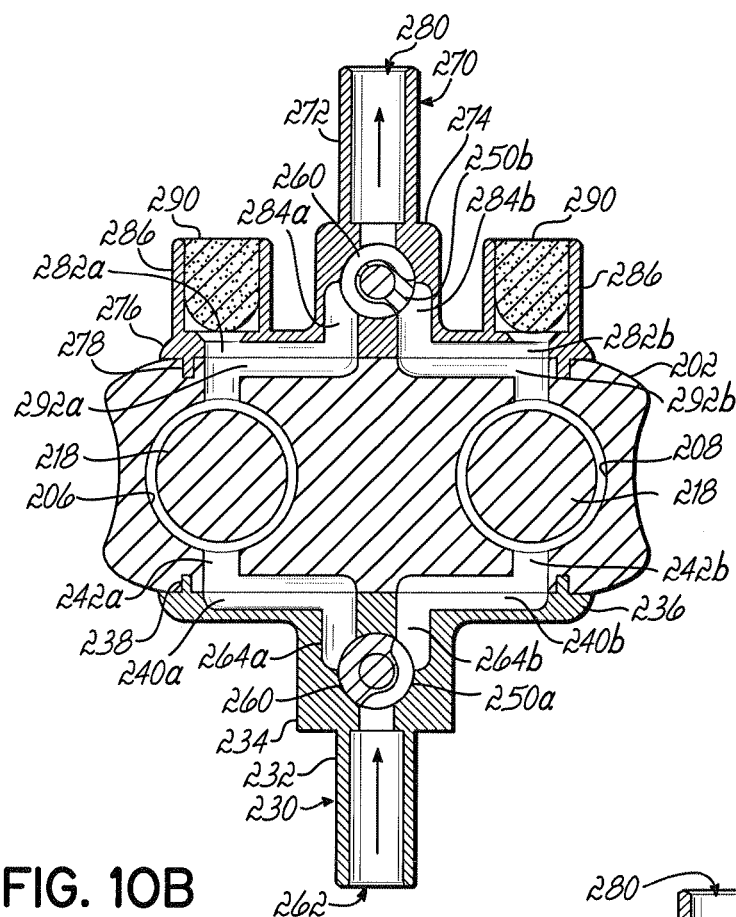
FIG. 10B is a cross-sectional view similar to FIG. 10A, but with the inlet and outlet valves rotated to positions wherein the second pump chamber is being filled with fluid and fluid is being pumped out of the first pump chamber.
Figure 10C:
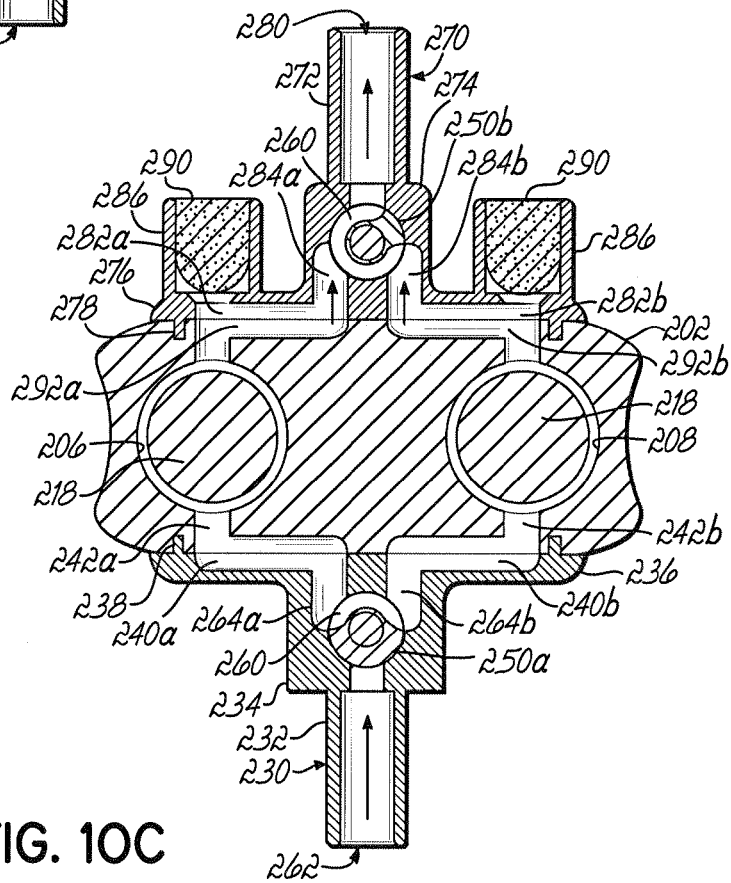
FIG. 10C is a cross-sectional view similar to FIG. 10A but with fluid being pumped out of both pump chambers.
Figure 11A:
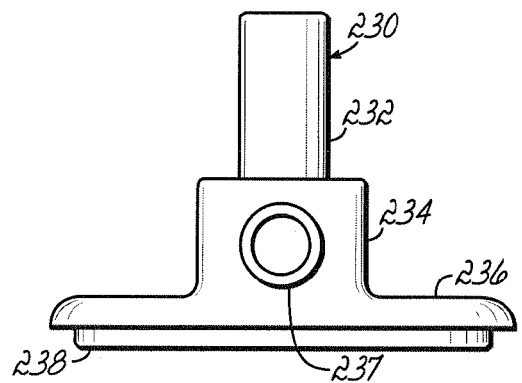
FIG. 11A is a side elevation view of the inlet manifold of the pump module shown in FIGS. 8-10C.
Figure 11B:
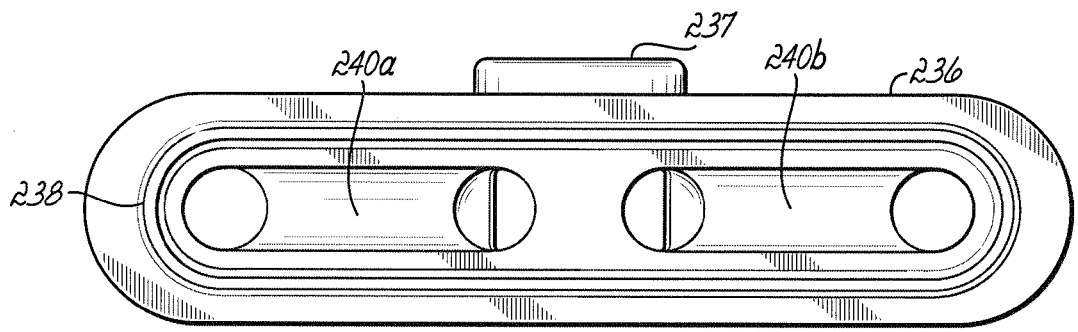
FIG. 11B is an enlarged bottom plan view of the inlet manifold shown in FIG. 11A.
Figure 12A:
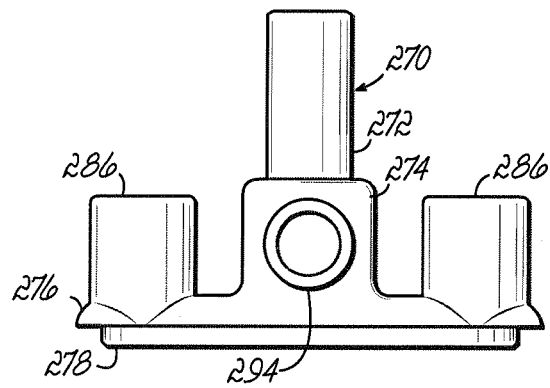
FIG. 12A is a side elevation view of the outlet manifold of the pump module shown in FIGS. 8-10C.
Figure 12B:
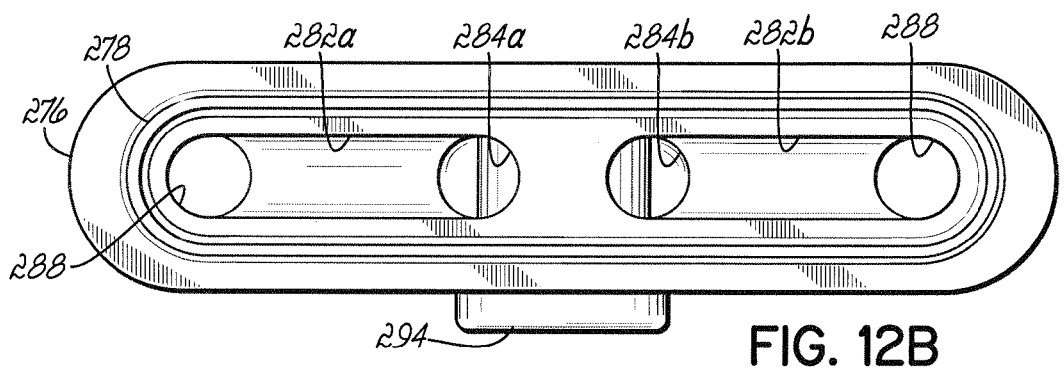
FIG. 12B is an enlarged bottom plan view of the outlet manifold shown in FIG. 12A.

As shown in FIGS. 8, 10A-10C and 11A and 11B, pump module 200 includes an inlet manifold 230 that is secured to pump body 202. Manifold 230 includes a coupling portion 232, an intermediate portion 234 integral with the coupling portion 232, and an elongated portion 236 integral with the intermediate portion. Elongated portion 236 is secured to pump body 202, which can be achieved in a variety of ways. In the illustrated embodiment, the elongated portion 236 includes a ridge 238 that is inserted into a mating recess formed in pump body 202. Elongated portion 236 of inlet manifold 230 includes a pair of fluid passages 240a, 240b formed therein that are aligned with mating passages 242a, 242b, respectively, that are formed in pump body 202, as best seen in FIGS. 10A-10C. One end of fluid passage 242a opens into pump chamber 206, while one end of fluid passage 242b opens into pump chamber 208.

Figure 13:
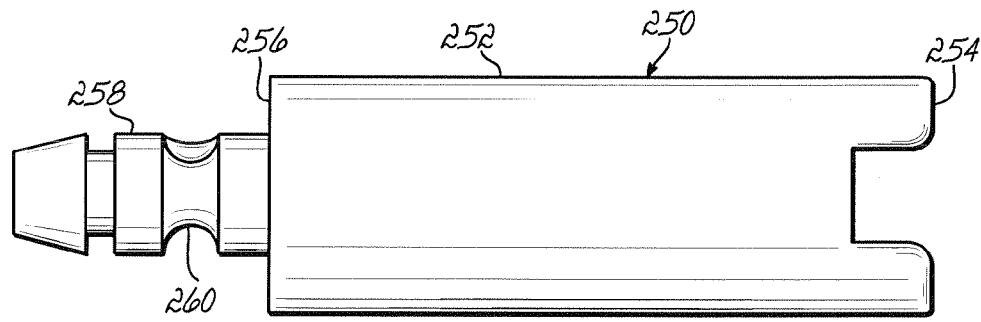
FIG. 13 is a side elevation view of one of the valves of the pump module shown in FIGS. 8-10C.

Pump module 200 further includes a pair of rotatable valves 250 shown in FIG. 13, with one of the valves 250 being an inlet valve and identified as valve 250a shown in FIGS. 10A-10C. The other valve 250 is an outlet valve and is identified as valve 250b in FIGS. 8 and 10A-10C. Each of the valves 250a, 250b include a barrel 252 having a proximal end 254 and a distal end 256. The proximal end 254 of each valve 250a, 250b is configured to facilitate coupling each valve 250a, 250b to a rotational actuator (as shown schematically in FIG. 14). Each valve 250a, 250b further includes a stem 258 integral with the distal end 256 of barrel 252. Stem 258 includes a circumferentially extending notch 260 that extends around a portion of the circumference of stem 258. The circumferential extent of notch 260 can vary. In the illustrated embodiment, the circumferential extent of notch 260 of inlet valve 250a is about 180°, while the circumferential extent of notch 260 of outlet valve 250b is about 330° to accommodate pumping out of one of the chambers 206, 208 at a time or pumping out of both of the chambers 206, 208 simultaneously as subsequently discussed. In other embodiments, the circumferential extent of notches 260 can be different than those discussed previously.

The coupling portion 232 and the intermediate portion 234 of inlet manifold 230 combine to define a fluid inlet 262 of pump module 250. Intermediate portion 234 further includes a fluid passage 264a in fluid communication with passage 240a of the elongated portion 236 and a second fluid passage 264b that is in fluid communication with the fluid passage 240b formed in the elongated portion 236. The stem 258 of the inlet valve 250a extends through the intermediate portion 234 of inlet manifold 230. The intermediate portion 234 includes a cylindrical protrusion 237 that supports stem 258.

The inlet valve 250a can be rotated to a first angular orientation, shown in FIG. 10A, wherein the fluid inlet 262 is in fluid communication with pump chamber 206. In this position, the circumferential notch 260 of inlet valve 250a is in fluid communication with the fluid inlet 262 and the fluid passage 264a. The inlet valve 250a can be rotated to a second angular orientation, shown in FIG. 10B, wherein the fluid inlet 262 is in fluid communication with the pump chamber 208. In this position, the circumferential notch 260 of inlet valve 250a is in fluid communication with the fluid inlet 262 and the fluid passage 264b. Additionally, the inlet valve 250a can be rotated to a third angular position shown in FIG. 10C, wherein the fluid inlet 262 is fluidicly uncoupled from both of the chambers 206, 208.

Pump module 200 further includes an outlet manifold 270 shown in FIGS. 8, 10A-10C and 12A, 12B. Outlet manifold 270 is secured to pump body 202. Outlet manifold 270 includes a coupling portion 272, an intermediate portion 274 integral with the coupling portion 272 and an elongated portion 276 that is integral with the intermediate portion 274. The coupling portion 272 and the intermediate portion 274 combine to define an outlet 280 of pump module 200. The elongated portion 276 is secured to the pump body 202, which can be achieved in a variety of ways. In the illustrated embodiment, the elongated portion 276 includes a ridge 278 that is inserted into a mating recess formed in pump body 202. The elongated portion 276 further includes a pair of fluid passages 282a and 282b formed therein. One end of passage 282a is in fluid communication with a passage 284a that extends into the intermediate portion 274 of outlet manifold 270. Similarly, one end of the fluid passage 282b is in fluid communication with a fluid passage 284b that extends into the intermediate portion 274 of outlet manifold 270.

Outlet manifold 270 further includes a pair of filter receptacles 286, each having a hollow interior 288. The opposite end of each fluid passage 282a, 282b is in fluid communication with the hollow interior 288 of one of the filter receptacles 286. Pump module 200 further includes a pair of porous air filters 290, with each of the filters 290 being inserted into the hollow interior 288 of one of the filter receptacles 286. Each of the filters 290 comprises a hydrophobic material that is effective for repelling water but allows air to pass therethrough.

Pump body 202 includes fluid passages 292a, 292b formed therein. The fluid passage 292a is aligned with and is in fluid communication with the fluid passage 282a of the elongated portion 276 of outlet manifold 270. Similarly, fluid passage 292b is aligned with and is in fluid communication with fluid passage 282b of outlet manifold 270. One end of the fluid passage 292a opens into pump chamber 206 so that fluid passage 292a is in fluid communication with pump chamber 206. Similarly, one end of fluid passage 292b opens into pump chamber 208 so that fluid passage 292b is in fluid communication with pump chamber 208.

The stem 258 of outlet valve 250b extends through the intermediate portion 274 of manifold 270. Intermediate portion 274 includes a cylindrical protrusion 294 that supports stem 258. The outlet valve 250b can be rotated to a first angular orientation, shown in FIG. 10B, wherein the fluid outlet 280 is in fluid communication with the pump chamber 206 but not with chamber 208. In this position, the circumferential notch 260 of outlet valve 250b is in fluid communication with the fluid outlet 280 and fluid passage 284a in the intermediate portion 274 of outlet manifold 270. The outlet valve 250b can be rotated to a second angular orientation, shown in FIG. 10A, wherein the fluid outlet 280 is in fluid communication with the pump chamber 208 but not with chamber 206. In this position, the circumferential notch 260 of outlet valve 250b is in fluid communication with the fluid outlet 280 and the fluid passage 284b formed in the intermediate portion 274 of outlet manifold 270. The outlet valve 250b can be rotated to a third angular orientation wherein the fluid outlet 280 is in fluid communication with both of the chambers 206, 208 as shown in FIG. 10C.

Figure 14:
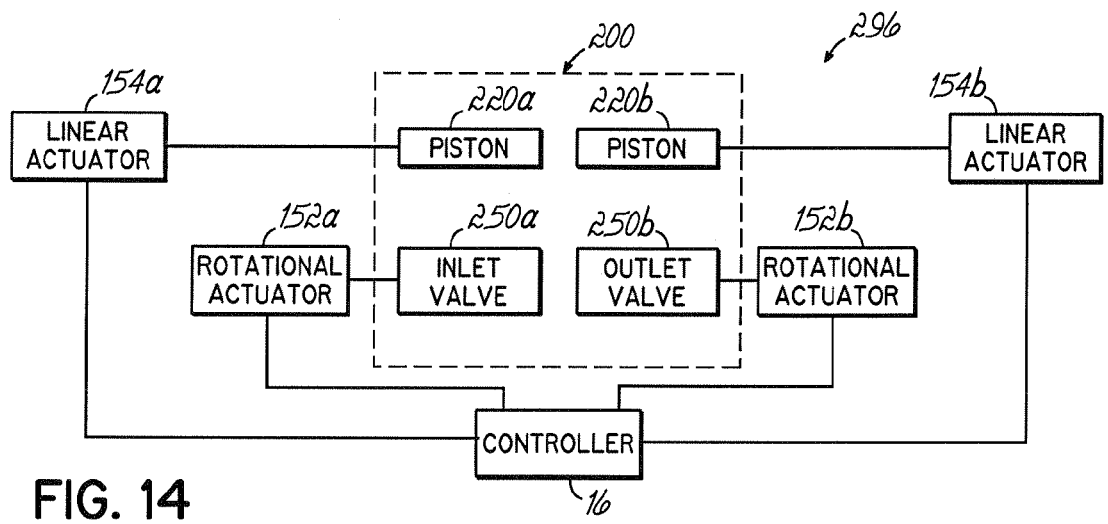
FIG. 14 is a schematic representation of a pump incorporating the pump module shown in FIGS. 8-13 and the corresponding control system.
Figure 15:
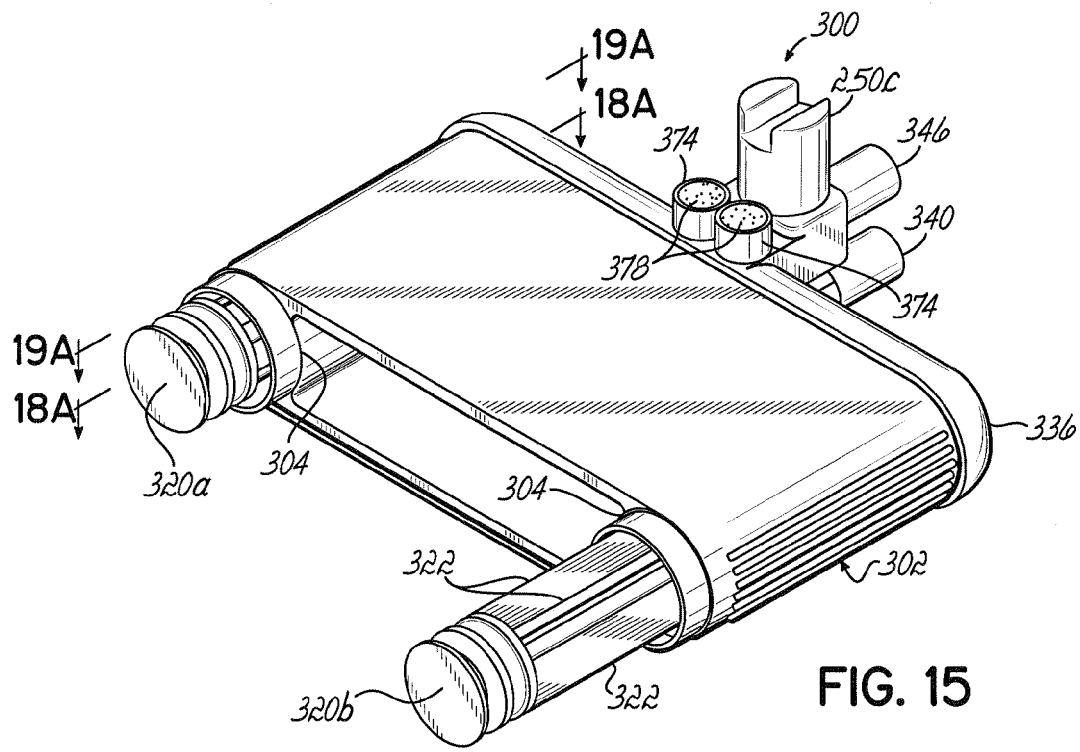
FIG. 15 is a perspective view of a pump module according to another embodiment of the present invention.
Figure 16:
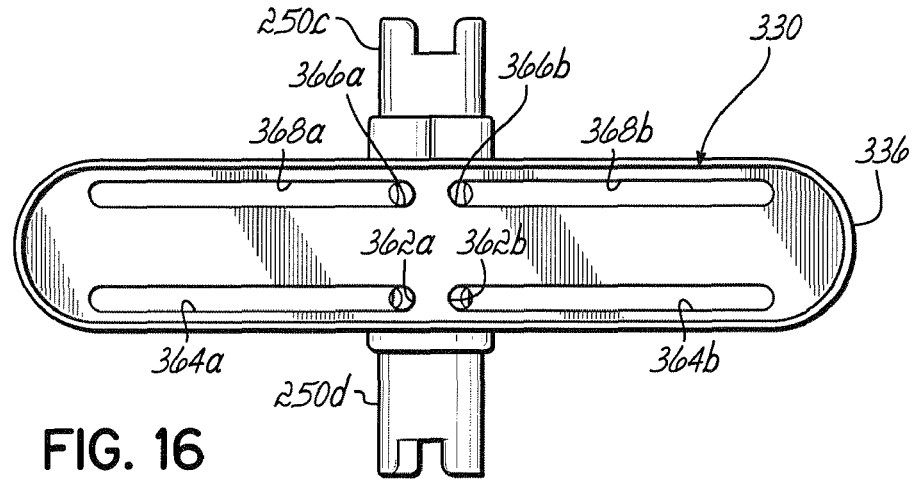
FIG. 16 is a bottom plan view of the manifold and inlet and outlet valves of the pump module shown in FIG. 15.
Figure 17:
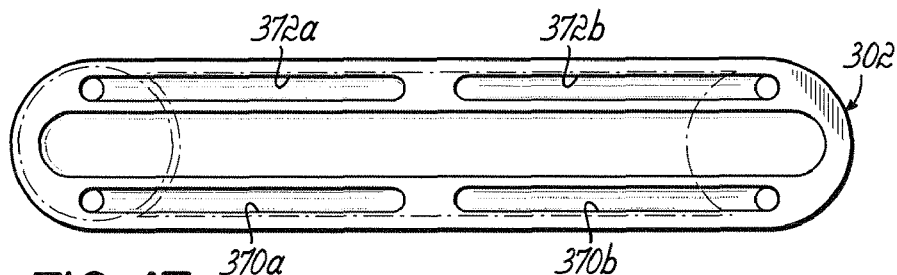
FIG. 17 is a top plan view of the body of the pump module shown in FIG. 15.

Pump module 200 can be included in a variety of pumps, such as pump 296 illustrated schematically in FIG. 14. In addition to pump module 200, pump 296 includes a pair of rotational actuators, such as actuators 152a and 152b included in pump 150 discussed previously. Pump 296 also includes a pair of linear actuators, such as actuators 154a, 154b that are also included in pump 150 discussed previously. Linear actuator 154a is mechanically coupled to piston 220a and can therefore be used to translate piston 220a within pump chamber 206. Similarly, the linear actuator 154b is mechanically coupled to piston 220b and can therefore be used to translate piston 220b within pump chamber 208. Rotational actuator 152a of pump 296 is mechanically coupled to inlet valve 250a and can therefore be used to rotate valve 250a to achieve the desired angular orientation of inlet valve 250a. Similarly, the rotational actuator 152b is mechanically coupled to outlet valve 250b and can therefore be used to rotate outlet valve 250b to the desired angular orientation.

The fluid inlet 262 can be fluidicly coupled to a source of medical fluid. For example, fluid inlet 262 can be fluidicly coupled to a source of medical fluid such as bag 20 illustrated schematically in FIG. 1, having a fluid 22 contained therein. The fluid outlet 280 can be fluidicly coupled to a patient via a section of tubing and a catheter, such as tubing 30 and catheter 34 illustrated schematically in FIG. 1.

The rotational actuators 152a and 152b are operated independently of one another and this can be accomplished with a programmable controller, such as controller 16. The linear actuators 154a, 154b are also operated independently of one another and this can also be accomplished with a programmable controller, such as controller 16. This allows fluid to be pumped out of one or both of the pump chambers 206, 208, at any given time. FIGS. 9A and 10A illustrate one phase of operation of pump 296. In this phase, the rotational actuator 152a rotates inlet valve 250a to a first angular orientation wherein the fluid inlet 262 is in fluid communication with pump chamber 206 and is fluidicly uncoupled with pump chamber 208, as shown in FIG. 10A. In this orientation, fluid inlet 262 is in fluid communication with fluid passage 264a. Piston 220a is retracted via linear actuator 154a, so that piston 220a translates away from the closed end 212 of pump chamber 206 as shown in FIG. 9A, thereby filling at least a portion of pump chamber 206 with medical fluid. At the same time, fluid is being pumped out of pump chamber 208. This can be accomplished as follows. The rotational actuator 152b rotates the outlet valve 250b to an angular orientation wherein the fluid outlet 280 is in fluid communication with pump chamber 208 and outlet 280 is fluidicly uncoupled with pump chamber 206 as shown in FIG. 10A. In this orientation, fluid outlet 280 is in fluid communication with the outlet passage 284b. Piston 220b is extended toward the closed end 216 of pump chamber 208 as shown in FIG. 9A so that fluid is pumped out of the pump chamber 208 and through fluid outlet 280.

The inlet face of the corresponding filter 290 is in fluid communication with the fluid being pumped out of chamber 208. The fluid does not pass through filter 290 due to the presence of a hydrophobic material. However, any air entrained within the fluid can pass through the filter 290 and discharge into the environment surrounding pump 296. In order to ensure a constancy of fluid flow, piston 220a can be translated toward the closed end 212 of pump chamber 206, just prior to the end of the pumping stroke of piston 220b. Accordingly, fluid can be pumped simultaneously out of both of the chambers 206, 208 and through the fluid outlet 280, as shown in FIG. 10C. In this phase of operation, the fluid inlet 262 is fluidicly uncoupled with both of the chambers 206, 208.

FIGS. 9B and 10B illustrate a phase of operation where fluid is being pumped out of pump chamber 206 and through fluid outlet 280, while pump chamber 208 is being at least partially filled with fluid. This is achieved by rotating the outlet valve 250b to an angular orientation wherein pump chamber 206 is in fluid communication with the fluid outlet 280, with pump chamber 208 being fluidicly uncoupled with outlet 280, and by rotating the inlet valve 250a to an angular orientation wherein the pump chamber 208 is in fluid communication with the fluid inlet 262 and pump chamber 206 is fluidicly uncoupled with inlet 262, as shown in FIG. 10B.

FIGS. 15-20 illustrate a pump module 300 according to another embodiment of the present invention. Pump module 300 includes a pump body 302 made of a non-compliant material. An example of a suitable material is a plastic material, such as a polycarbonate. As shown in FIGS. 18A-19C, the pump body 302 includes a pair of laterally spaced cylinders 304 that define pump chambers 306 and 308. Chamber 306 includes a first, open end 310 and an opposite, closed end 312. Similarly, pump chamber 308 includes a first, open end 314 and an opposite, closed end 316. The closed ends 312, 316 of pump chambers 306, 308 respectively are defined by a transverse wall 318 of the respective cylinder 304. Transverse walls 318 are made of the same non-compliant material as the remainder of pump body 302.

Pump module 300 further includes a pair of pistons, designated as 320a and 320b, which are disposed in the pump chambers 306 and 308, respectively. Pistons 320a, 320b can be made of HDPE, due to the lubricity of this material, or other suitable materials. In the illustrated embodiment, pistons 320a, 320b include a plurality of longitudinally extending and circumferentially spaced fins 322. However, in other embodiments, pistons 320a, 320b can include a cylindrical portion in lieu of the fins 322. Piston 320a is translatable within pump chamber 306 toward and away from the closed end 312 of chamber 306 and piston 320b is translatable within pump chamber 308 toward and away from the closed end 316 of pump chamber 308. Pump module 300 can further include a pair of covers or seals (not shown) in surrounding relationship with a portion of pistons 320a, 320b, similar to those illustrated in previously described embodiments, which can be used to prevent pistons 320a, 320b from being contaminated by the surrounding environment.

Unlike the previously discussed embodiments which include at least one inlet manifold and an outlet manifold, pump module 300 includes a single manifold 330 that functions as both an inlet manifold and an outlet manifold. Manifold 330 includes a first coupling portion 332 (shown in FIGS. 18A-18C), a first intermediate portion 334 integral with the coupling portion 332 and an elongated portion 336 that is integral with the intermediate portion 334 and is secured to pump body 302. The first coupling portion 332 defines a fluid inlet 340 of pump module 300. Manifold 330 further includes a second coupling portion 342 (shown in FIGS. 19A-19C) and a second intermediate portion 344 that is integral with the second coupling portion 342 and with the elongated portion 336. The second coupling portion 342 defines a fluid outlet 346 of pump module 300.

Pump module 300 further includes a pair of rotatable valves 250, shown in FIGS. 15, 16 and 18A-19C with one of the valves 250 being an inlet valve and identified as valve 250c and the other valve 250 being an outlet valve and identified as valve 250d. Valves 250c and 250d can be the same as valves 250a and 250b discussed previously and shown in a side elevation view in FIG. 13, with the following exceptions. The barrels 252 of valves 250c and 250d can be shorter than the barrels 252 of valves 250a and 250b and the frustoconical end of stem 258, which is spaced apart from barrel 252, of valves 250a and 250b can be omitted in valves 250c and 250d to accommodate the configuration of pump module 300 as compared to the configuration of pump module 200. As with valves 250a, 250b, the proximal end 254 of each valve 250c, 250d is configured to facilitate coupling each valve 250c, 250d to a rotational actuator (as shown schematically in FIG. 20). Similar to inlet valve 250a, the circumferential extent of the notch 260 in inlet valve 250c is about 180° in the illustrated embodiment. Also, similar to outlet valve 250b, the circumferential extent of the notch 260 in outlet valve 250d is about 330° in the illustrated embodiment to accommodate pumping out of one or both of the pump chambers 306, 308 at any given time. However, in other embodiments, the circumferential extent of notches 260 can be different than those discussed previously.

Referring to FIGS. 16 and 18A-18C, the first intermediate portion 334 includes fluid passages 362a, 362b formed therein. Elongated portion 336 of manifold 330 includes inlet passages 364a, 364b formed therein. Inlet passage 364a is in fluid communication with the passage 362a in intermediate portion 334 and the inlet passage 364b is in fluid communication with passage 362b formed in the intermediate portion 334.

Referring to FIGS. 16 and 19A-19C, the second intermediate portion 344 includes fluid passages 366a, 366b formed therein. Elongated portion 336 of manifold 330 further includes fluid outlet passages 368a, 368b formed therein. The fluid outlet passage 368a is in fluid communication with fluid passage 366a and the fluid outlet passage 368b is in fluid communication with the fluid passage 366b.

As shown in FIGS. 17 and 18A-19C, pump body 302 includes fluid passages 370a and 370a formed therein, each having one end opening into pump chamber 306 so that passages 370a, 370a are in fluid communication with pump chamber 306. Body 302 further includes passages 370b and 370b formed therein, each having one end opening into pump chamber 308 so that passages 370b, 370b are in fluid communication with pump chamber 308. Fluid inlet passages 364a, 364b formed in manifold 330 are aligned with and are in fluid communication with passages 370a, 370b, respectively, formed in body 302. Fluid outlet passages 368a, 368b formed in manifold 330 are aligned with and are in fluid communication with the passages 370a, 370b, respectively, formed in body 302.

The manifold 330 further includes a pair of filter receptacles 374, each having a hollow interior. A porous air filter 378 is disposed in the hollow interior of each one of the receptacles 374. Each filter 378 can comprise a hydrophobic material. The inlet face of each filter 378 is in fluid communication with one of the fluid outlet passages 368a, 368b formed in manifold 330.

The stem 258 of inlet valve 250c extends through an aperture formed in the first intermediate portion 334 of manifold 330. The stem 258 of outlet valve 250d extends through an aperture formed in the second intermediate portion 344 of manifold 330. The inlet valve 250c can be rotated to a first angular orientation, shown in FIG. 18A, wherein the fluid inlet 340 is in fluid communication with pump chamber 306. In this position, the circumferential notch 260 of inlet valve 250c is in fluid communication with fluid inlet 340 and the fluid passage 362a formed in the first intermediate portion 334. The inlet valve 250c can be rotated to a second angular orientation, shown in FIG. 18B, wherein the fluid inlet 340 is in fluid communication with the pump chamber 308. In this position, the circumferential notch 260 of inlet valve 250c is in fluid communication with the fluid inlet 340 and the fluid passage 362b formed in the first intermediate portion 334 of manifold 330. Additionally, the inlet valve 250c can be rotated to a third angular orientation shown in FIG. 18C where the fluid inlet 340 is fluidicly uncoupled with both of the pump chambers 306, 308.

Figure 19A:
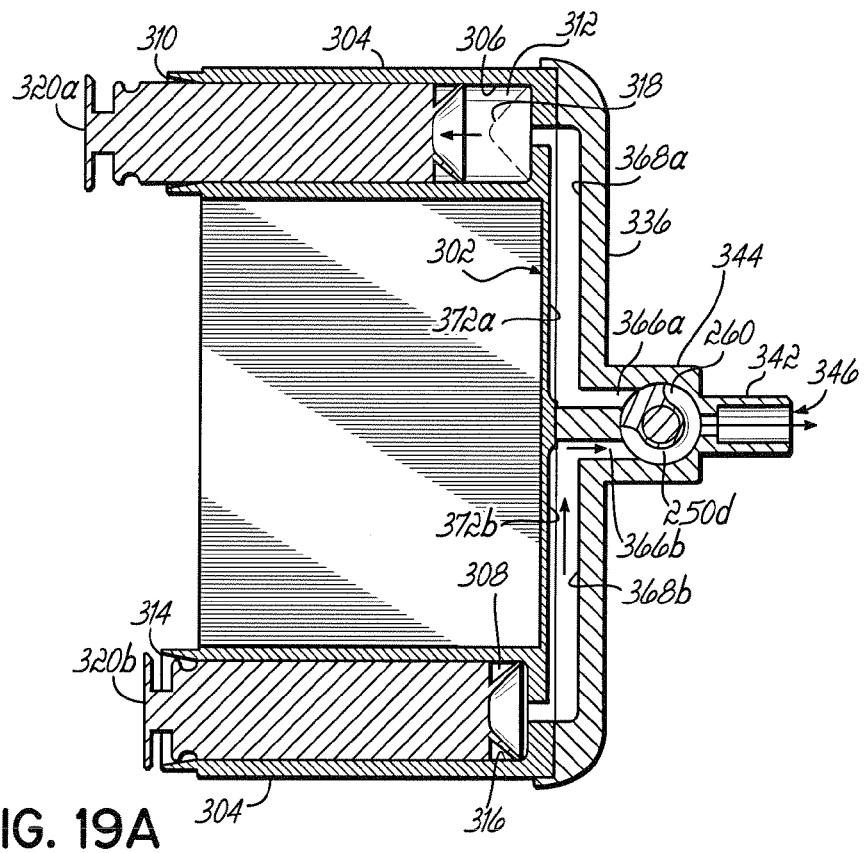
FIG. 19A is a cross-sectional view taken along line 19A-19A in FIG. 15 illustrating the first pump chamber fluidicly uncoupled with the fluid outlet and with fluid being pumped out of the second pump chamber through the fluid outlet.
Figure 19B:
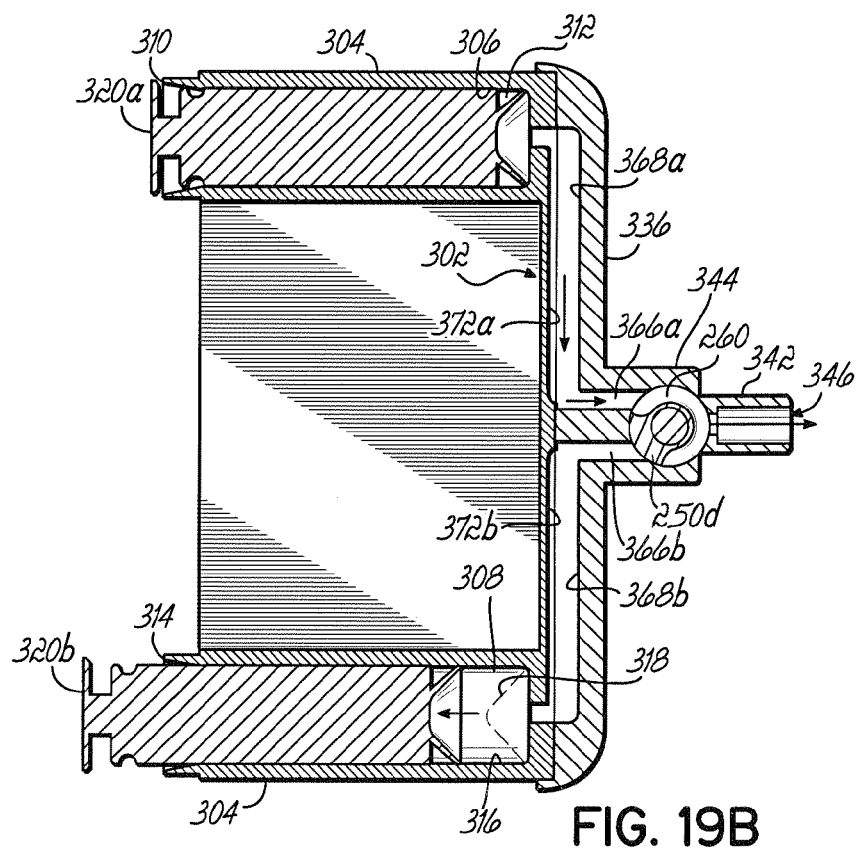
FIG. 19B is a cross-sectional view similar to FIG. 19A but with fluid being pumped out of the first pump chamber through the fluid outlet and with the second pump chamber fluidicly uncoupled with the fluid outlet.

The outlet valve 250d can be rotated to a first angular orientation, shown in FIG. 19B, wherein the fluid outlet 346 is in fluid communication with pump chamber 306. In this position, the circumferential notch 260 of outlet valve 250d is in fluid communication with fluid outlet 346 and the fluid passage 366a formed in the second intermediate portion 344 of manifold 330. The outlet valve 250d can be rotated to a second angular orientation, shown in FIG. 19A, wherein the fluid outlet 346 is in fluid communication with the pump chamber 308. In this position, the circumferential notch 260 of outlet valve 250d is in fluid communication with the fluid outlet 346 and the fluid passage 366b formed in the second intermediate portion 344 of manifold 330.

Figure 20:
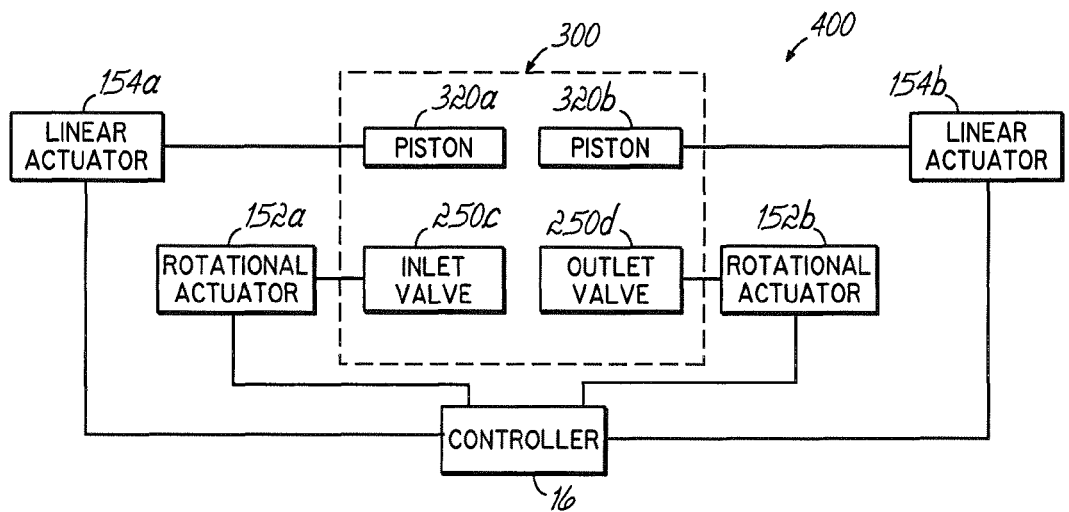
FIG. 20 is a schematic representation of a pump incorporating the pump module shown in FIGS. 15-19 and the corresponding control system.

Pump module 300 can be included in a variety of pumps, such as pump 400 illustrated schematically in FIG. 20. In addition to pump module 300, pump 400 includes a pair of rotational actuators, such as actuators 152a and 152b included in pumps 150 and 296 discussed previously. Pump 400 also includes a pair of linear actuators, such as actuators 154a, 154b that are also included in pumps 150, 296 discussed previously. Linear actuator 154a of pump 400 is mechanically coupled to piston 320a and can therefore be used to translate piston 320a within pump chamber 306. Similarly, the linear actuator 154b is mechanically coupled to piston 320b and can therefore be used to translate piston 320b within pump chamber 308. Rotational actuator 152a of pump 400 is mechanically coupled to inlet valve 250c and can therefore be used to rotate inlet valve 250c to achieve the desired angular orientation. Similarly, the rotational actuator 152b is mechanically coupled to outlet valve 250d and can therefore be used to rotate outlet valve 250d to the desired angular orientation.

Fluid inlet 340 can be fluidicly coupled to a source of medical fluid. For example, fluid inlet 340 can be fluidicly coupled to a source of medical fluid such as bag 20 illustrated schematically in FIG. 1, having a fluid 22 contained therein. Fluid outlet 346 can be fluidicly coupled to a patient via a section of tubing and a catheter, such as tubing 30 and catheter 34 illustrated schematically in FIG. 1.

Figure 18A:
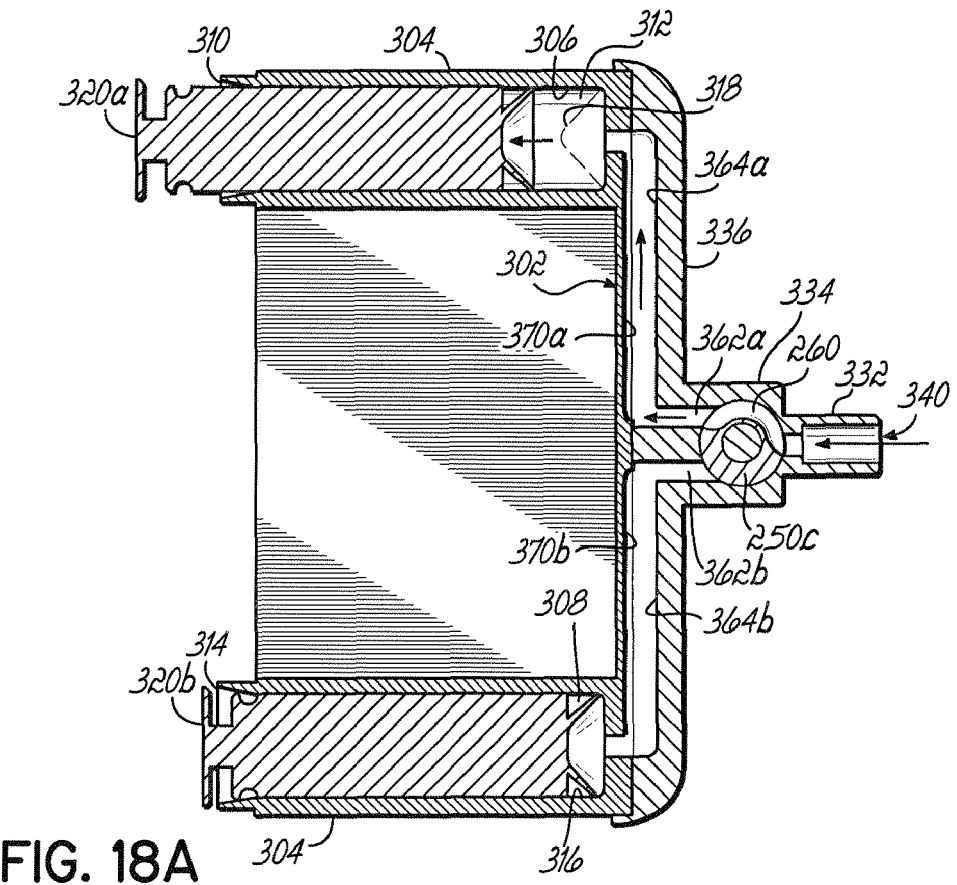
FIG. 18A is a cross-sectional view taken along line 18A-18A in FIG. 15 illustrating a first one of the pump chambers in fluid communication with the fluid inlet so that the first pump chamber is at least partially filled with fluid, and further illustrating the second pump chamber fluidicly uncoupled with the fluid inlet.

The rotational actuators 152a and 152b are operated independently of one another and this can be accomplished with a programmable controller, such as controller 16 as discussed previously with respect to pump 296. The linear actuators 154a and 154b are also operated independently of one another and this can also be accomplished with a programmable controller, such as controller 16. This allows fluid to be pumped out of one or both of the pump chambers 306, 308, at any given time. FIGS. 18A and 19A illustrate one phase of operation of pump 400. In this phase, the rotational actuator 152a rotates inlet valve 250c to an angular orientation shown in FIG. 18A wherein the fluid inlet 340 is in fluid communication with pump chamber 306 and is fluidicly uncoupled with pump chamber 308. Piston 320a is retracted via linear actuator 154a, so that piston 320a translates away from the closed end 312 of pump chamber 306, thereby filling at least a portion of pump chamber 306 with medical fluid. At the same time, fluid is being pumped out of pump chamber 308. This can be accomplished as follows. The rotational actuator 152b rotates the outlet valve 250d to an angular orientation shown in FIG. 19A wherein the fluid outlet 346 is in fluid communication with pump chamber 308 and is fluidicly uncoupled with pump chamber 306. Piston 320b is extended toward the closed end 316 of pump chamber 308 so that fluid is pumped out of pump chamber 308 and through fluid outlet 346.

Figure 19C:
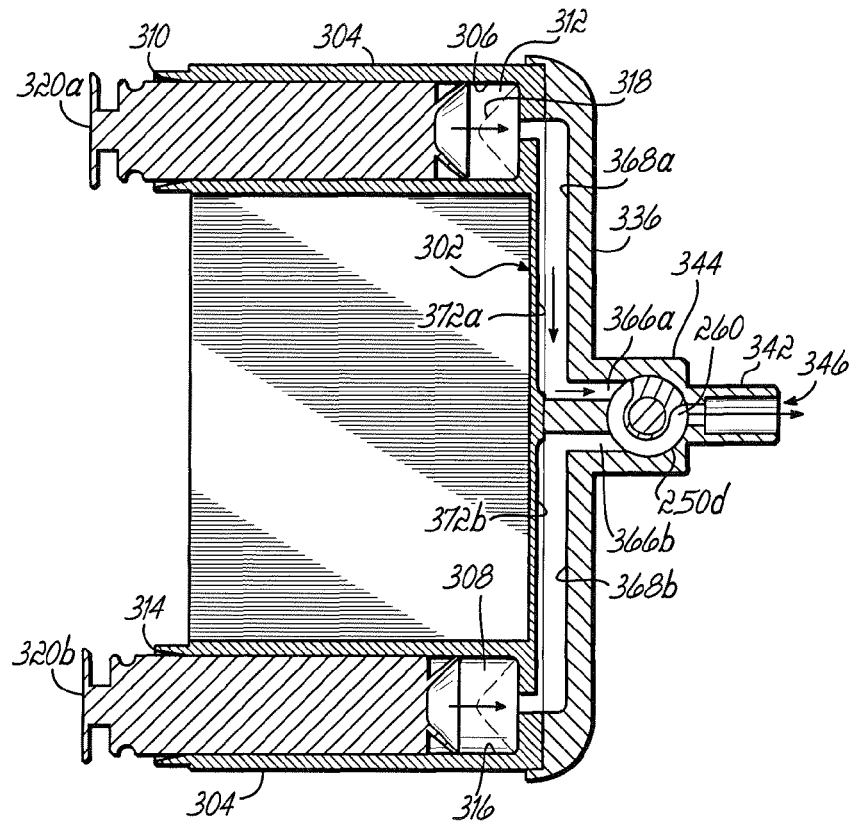
FIG. 19C is a cross-sectional view similar to FIG. 19A but with fluid being pumped out of both of the pump chambers and through the fluid outlet simultaneously.

The inlet face of the corresponding filter 378 is in fluid communication with the fluid being pumped out of chamber 308. The fluid does not pass through filter 378 due to the presence of the hydrophobic material. However, any air entrained within the fluid can pass through the filter 378 and discharge into the environment surrounding pump 400. In order to ensure a constancy of fluid flow, the outlet valve 250d can be rotated to a third angular orientation shown in FIG. 19C where both chambers 306, 308 are in fluid communication with outlet 346, and piston 320a can be translated toward the closed end 312 of pump chamber 306, just prior to the end of the pumping stroke of piston 320b. Accordingly, fluid can be pumped simultaneously out of both of the chambers 306, 308 and through the fluid outlet 346, as shown in FIG. 19C. During this phase of operation, the inlet valve 250c can be rotated to the angular orientation shown in FIG. 18C where the fluid inlet 340 is fluidicly uncoupled with both of the chamber 206, 208.

Figure 18B:
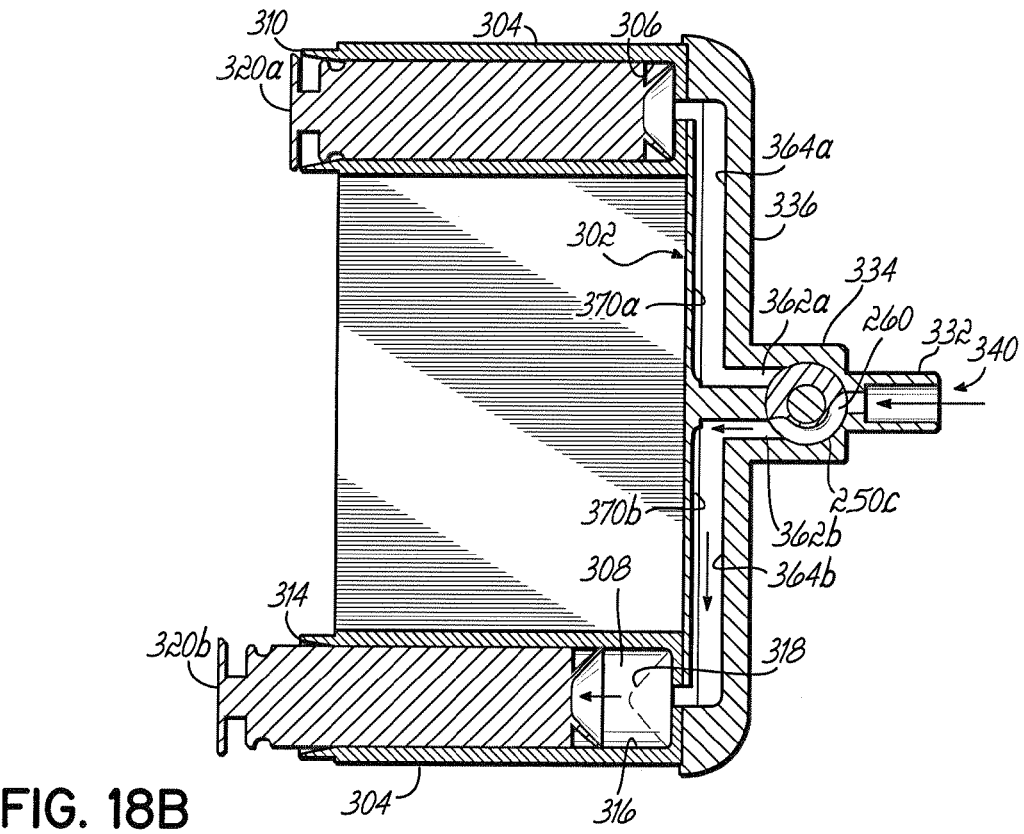
FIG. 18B is a cross-sectional view similar to FIG. 18A but with the first pump chamber fluidicly uncoupled with the fluid inlet and with the second pump chamber in fluid communication with the fluid inlet so that the second pump chamber is at least partially filled with fluid.
Figure 18C:
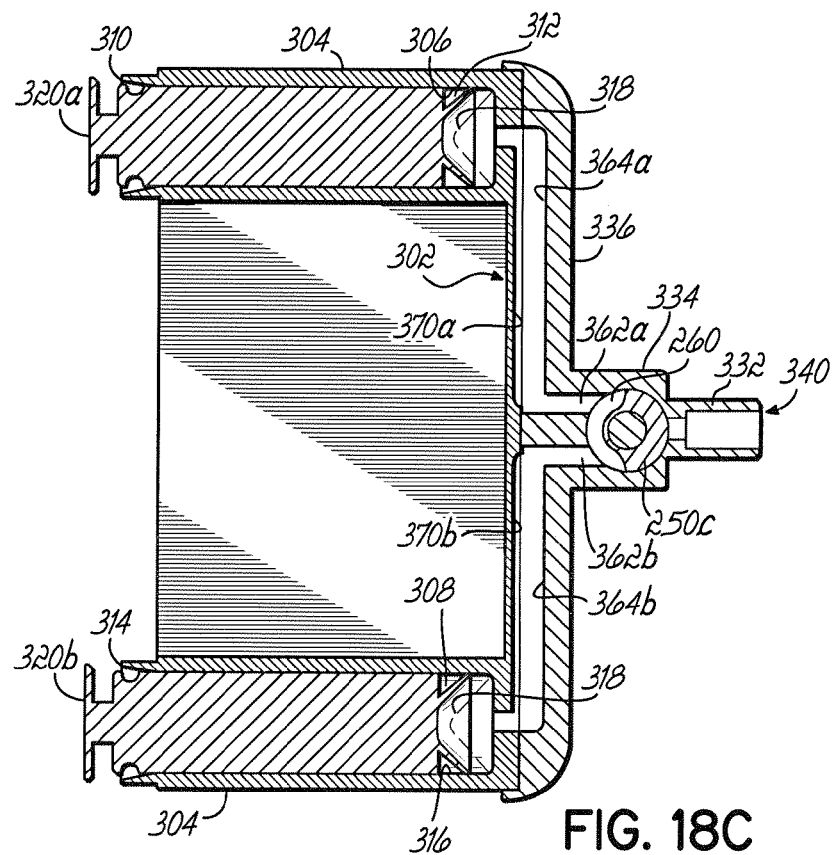
FIG. 18C is a cross-sectional view similar to FIG. 18A but with both the first and second pump chambers fluidicly uncoupled with the fluid inlet.

FIGS. 18B and 19B illustrate a phase of operation wherein fluid is being pumped out of pump chamber 306 and through fluid outlet 346, while pump chamber 308 is being at least partially filled with fluid. This is achieved by rotating the outlet valve 250d to an angular orientation wherein pump chamber 306 is in fluid communication with the fluid outlet 346 as shown in FIG. 19B, with chamber 308 being fluidicly uncoupled with outlet 346, and by rotating the inlet valve 250c to an angular orientation wherein the pump chamber 308 is in fluid communication with the fluid inlet 340 and the pump chamber 306 is fluidicly uncoupled with inlet 340, as shown in FIG. 18B.

While the foregoing description has set forth various embodiments of the present invention in particular detail, it must be understood that numerous modifications, substitutions and changes can be undertaken without departing from the true spirit and scope of the present invention as defined by the ensuing claims. Pumps in accordance with the principles of the present invention can be used in a variety of applications, ranging from low to high volume fluid applications. However, pumps in accordance with the principles of the present invention have particularly advantageous use in high volume fluid applications. The invention is therefore not limited to specific embodiments as described, but is only limited as defined by the following claims.

What is claimed is:

1. A pump module for use in a medical fluid dispensing system comprising:
   a pump body made of a non-compliant material;
   first and second pump chambers formed in said body, each of said chambers having a first, open end and an opposite, closed end;
   first and second pistons in said first and second pump chambers, respectively;
   at least one fluid inlet selectively in fluid communication with said first and second pump chambers;
   a fluid outlet selectively in fluid communication with said first and second pump chambers; wherein
   each of said pistons extends through said open end of a respective one of said pump chambers, each of said pistons being operably translatable within said respective one of said pump chambers toward and away from said closed end of said respective one of said pump chambers, said pistons being translatable independently of one another.

2. A pump module as recited in claim 1, wherein:
said first piston is translatable and rotatable within said first pump chamber and said second piston is translatable and rotatable within said second pump chamber.

3. A pump module as recited in claim 2, wherein:
said at least one fluid inlet comprises a single fluid inlet;
said first piston is rotatable to a first angular orientation wherein said single fluid inlet is in fluid communication with said first pump chamber and is rotatable to a second angular orientation wherein said fluid outlet is in fluid communication with said first pump chamber;
said second piston is rotatable to a first angular orientation wherein said single fluid inlet is in fluid communication with said second pump chamber and is rotatable to a second angular orientation wherein said fluid outlet is in fluid communication with said second pump chamber.

4. A pump module as recited in claim 2, wherein:
said at least one fluid inlet comprises first and second fluid inlets, each being selectively in fluid communication with said first and second pump chambers.

5. A pump module as recited in claim 2, wherein:
each of said pistons comprises a longitudinally extending channel formed therein and in fluid communication with a corresponding one of said pump chambers, each of said channels being selectively in fluid communication with said at least one fluid inlet and said fluid outlet.

6. A pump module as recited in claim 1, wherein:
said first and second pistons are disposed in opposing relationship with one another.

7. A pump module as recited in claim 6, wherein:
said body comprises a transverse wall separating said first and second pump chambers.

8. A pump module as recited in claim 1, wherein:
said pump body is made of a plastic material.

9. A pump module as recited in claim 1, further comprising:
a pair of porous air filters, each comprising a hydrophobic material and each being in fluid communication with one of said pump chambers, wherein each of said filters is operably effective for allowing any air entrained within a fluid being pumped out of a corresponding one of said pump chambers to pass through said filter and discharge from said pump module.

10. A pump module as recited in claim 1, wherein:
said at least one fluid inlet comprises first and second fluid inlets;
said pump module further comprises first and second inlet manifolds and an outlet manifold;
said first and second inlet manifolds define said first and second fluid inlets, respectively, and said outlet manifold defines said fluid outlet.

11. A pump module as recited in claim 1, wherein:
said at least one fluid inlet comprises a single fluid inlet;
said pump module further comprises an inlet manifold and an outlet manifold;
said inlet manifold defines said single fluid inlet and said outlet manifold defines said fluid outlet.

12. A pump module as recited in claim 1, wherein:
said pistons are disposed in a side-by-side relationship with one another.

13. A pump module as recited in claim 12, wherein:
said pump body comprises a pair of laterally spaced cylinders formed therein, each of said cylinders defining one of said pump chambers.

14. A pump module as recited in claim 1, further comprising:
an inlet manifold and an outlet manifold; and
an inlet valve and an outlet valve; wherein
said at least one fluid inlet comprises a single fluid inlet, said inlet manifold defining said fluid inlet, said outlet manifold defining said fluid outlet;
said inlet valve comprises a stem extending into said inlet manifold downstream of said single fluid inlet and upstream of said pump chambers;
said outlet valve comprises a stem extending into said outlet manifold downstream of said pump chambers and upstream of said fluid outlet.

15. A pump module as recited in claim 1, further comprising:
an inlet valve and an outlet valve, each comprising a rotatable valve; wherein
said at least one fluid inlet comprises a single fluid inlet;
said inlet valve is rotatable to a first angular orientation wherein said first pump chamber is in fluid communication with said single fluid inlet and is rotatable to a second orientation wherein said second pump chamber is in fluid communication with said single fluid inlet;
said outlet valve is rotatable to a first angular orientation wherein said first pump chamber is in fluid communication with said fluid outlet and is rotatable to a second angular orientation wherein said second pump chamber is in fluid communication with said fluid outlet.

16. A pump module as recited in claim 1, further comprising:
a manifold, said manifold defining said at least one fluid inlet and said fluid outlet.

17. A pump module as recited in claim 16, further comprising:
an inlet valve having a stem, said stem extending into said manifold downstream of said at least one fluid inlet and upstream of said pump chambers;
an outlet valve having a stem, said stem extending into said manifold downstream of said pump chambers and upstream of said fluid outlet.

18. A pump module as recited in claim 17, wherein:
said inlet and outlet valves are rotatable valves;
said at least one fluid inlet comprises a single fluid inlet;
said inlet valve is rotatable to a first angular orientation wherein said single fluid inlet is in fluid communication with said first pump chamber and is rotatable to a second angular orientation wherein said single fluid inlet is in fluid communication with said second pump chamber; and
said outlet valve is rotatable to a first angular orientation wherein said fluid outlet is in fluid communication with said first pump chamber and is rotatable to a second angular orientation wherein said fluid outlet is in fluid communication with said second pump chamber.

19. A pump comprising:
a pump body made of a non-compliant material;
first and second pump chambers formed in said body, each of said chambers having a first, open end and an opposite, closed end;
first and second pistons in said first and second pump chambers, respectively;
a fluid inlet selectively in fluid communication with said first and second pump chambers;
a fluid outlet selectively in fluid communication with said first and second pump chambers;
first and second linear actuators coupled to said first and second pistons, respectively; wherein each of said pistons extends through said open end of a respective one of said pump chambers;

said first linear actuator is operable for translating said first piston within said first pump chamber toward and away from said closed end of said first pump chamber;

said second linear actuator is operable for translating said second piston within said second pump chamber toward and away from said closed end of said second pump chamber; and said first and second linear actuators are operable independently of one another wherein said first and second pistons are translatable independently of one another.

20. A pump as recited in claim 19, further comprising:
first and second rotational actuators.

21. A pump as recited in claim 20, wherein:
said first piston is mechanically coupled to said first rotational actuator, wherein said first piston is translatable and rotatable within said first pump chamber;
said second piston is mechanically coupled to said second rotational actuator, wherein said second piston is translatable and rotatable within said second pump chamber.

22. A pump as recited in claim 20, wherein:
said first rotational actuator is mechanically coupled to said first piston and is operable for rotating said first position to a first angular orientation wherein said first pump chamber is in fluid communication with said fluid inlet and is operable for rotating said first piston to a second angular orientation wherein said first pump chamber is in fluid communication with said fluid outlet;
said second rotational actuator is mechanically coupled to said second piston, wherein said second rotational actuator is operable for rotating said second piston to a first angular orientation wherein said second pump chamber is in fluid communication with said fluid inlet and is operable for rotating said second piston to a second angular orientation wherein said second pump chamber is in fluid communication with said fluid outlet.

23. A pump as recited in claim 20, further comprising:
an inlet valve and an outlet valve; wherein
said first rotational actuator is mechanically coupled to said inlet valve and is operable for rotating said inlet valve to a first angular orientation wherein said fluid inlet is in fluid communication with said first pump chamber and is operable for rotating said inlet valve to a second angular orientation wherein said fluid inlet is in fluid communication with said second pump chamber;
said second rotational actuator is mechanically coupled to said outlet valve, wherein said second rotational actuator is operable for rotating said outlet valve to a first angular orientation wherein said fluid outlet is in fluid communication with said first pump chamber, and is operable for rotating said outlet valve to a second angular orientation wherein said fluid outlet is in fluid communication with said second pump chamber.

24. A system for dispensing medical fluids intravenously to a patient comprising:
a pump; and
a programmable controller; wherein said pump comprises:
a pump body made of a non-compliant material;
first and second pump chambers formed in said body, each of said chambers having a first, open end and an opposite, closed end;
first and second pistons in said first and second pump chambers, respectively;
a fluid inlet selectively in fluid communication with said first and second pump chambers;
a fluid outlet selectively in fluid communication with said first and second pump chambers;
first and second linear actuators coupled to said first and second pistons, respectively; and wherein each of said pistons extends through said open end of a respective one of said pump chambers;

said first linear actuator is operable for translating said first piston within said first pump chamber toward and away from said closed end of said first pump chamber;

said second linear actuator is operable for translating said second piston within said second pump chamber toward and away from said closed end of said second pump chamber; and said first and second linear actuators are controlled independently of one another by said programmable controller such that said first and second pistons are translatable independently of one another.

25. A system as recited in claim 24, further comprising:
a first rotational actuator mechanically coupled to said first piston;
a second rotational actuator mechanically coupled to said second piston; wherein
said first and second rotational actuators are controlled independently of one another by said controller.

26. A system as recited in claim 24, further comprising:
inlet and outlet valves;
a first rotational actuator mechanically coupled to said inlet valve; and
a second rotational actuator mechanically coupled to said outlet valve; wherein
said first and second rotational actuators are controlled independently of one another by said controller.

* * * * *

UNITED STATES PATENT AND TRADEMARK OFFICE
CERTIFICATE OF CORRECTION

PATENT NO.         : 7,951,112 B2
APPLICATION NO.    : 11/749313
DATED              : May 31, 2011
INVENTOR(S)        : Charles R. Patzer Page 1 of 1

It is certified that error appears in the above-identified patent and that said Letters Patent is hereby corrected as shown below:

Column 3, line 59, "chambers have" should be -- chambers has --

Column 5, line 51, "medical outlet" should be -- fluid outlet --

Column 6, line 42, "FIG. 9A-9A" should be -- FIG. 9A --

Column 10, line 23, "fluid inlet 1 00" should be -- fluid inlet 100 --

Column 12, lines 33-34, "include a barrel" should be -- includes a barrel --

Column 18, lines 23-24, "both of the chamber" should be -- both of the chambers --

Claim 22, column 21, line 24 "rotating said first position" should be -- rotating said first piston --

Signed and Sealed this
Ninth Day of August, 2011

David J. Kappos
*Director of the United States Patent and Trademark Office*